United States Patent [19]

Fant et al.

[11] Patent Number: 4,519,041

[45] Date of Patent: May 21, 1985

[54] REAL TIME AUTOMATED INSPECTION

[75] Inventors: Karl M. Fant, Minneapolis; Richard A. Fundakowski, Saint Paul; Tod S. Levitt, Minneapolis; John E. Overland, Plymouth; Bindinganavle R. Suresh, New Brighton; Franz W. Ulrich, Minneapolis, all of Minn.

[73] Assignee: Honeywell Inc., Minneapolis, Minn.

[21] Appl. No.: 374,373

[22] Filed: May 3, 1982

[51] Int. Cl.³ .................. G06F 15/20; G06F 15/46; G06G 7/48

[52] U.S. Cl. .................. 364/552; 364/469; 382/22; 382/54

[58] Field of Search ........... 364/468, 469, 474, 476, 364/550, 552, 507, 472; 382/8, 16, 21, 22, 54; 356/429–431

[56] References Cited

U.S. PATENT DOCUMENTS

| 4,097,845 | 6/1978 | Bacus | 382/21 |
| 4,131,490 | 12/1978 | Oishi et al. | 364/472 |
| 4,223,346 | 9/1980 | Neiheisel et al. | 356/430 |
| 4,361,830 | 11/1982 | Honma et al. | 382/22 |
| 4,403,294 | 9/1983 | Hamada et al. | 364/507 |

Primary Examiner—James D. Thomas
Assistant Examiner—Dale M. Shaw
Attorney, Agent, or Firm—Charles G. Mersereau; Wayne B. Easton

[57] ABSTRACT

A method and apparatus relating to the real time automatic detection and classification of characteristic type surface imperfections occurring on the surfaces of material of interest such as moving hot metal slabs produced by a continuous steel caster. A data camera transversely scans continuous lines of such a surface to sense light intensities of scanned pixels and generates corresponding voltage values. The voltage values are converted to corresponding digital values to form a digital image of the surface which is subsequently processed to form an edge-enhanced image having scan lines characterized by intervals corresponding to the edges of the image. The edge-enhanced image is thresholded to segment out the edges and objects formed by the edges are segmented out by interval matching and bin tracking. Features of the objects are derived and such features are utilized to classify the objects into characteristic type surface imperfections.

24 Claims, 43 Drawing Figures

1. LONGITUDINAL FACE CRACKS
    A. HEAVY
    B. MEDIUM
    C. FINE
2. LONGITUDINAL CORNER CRACKS
3. TRANSVERSE FACE CRACKS (TEARS)
    A. HEAVY
    B. FINE (OFTEN IN OSCILLATOR GROOVES)
4. SCUM PATCH, SCUM PITS
5. SCUM TEAR
6. EDGE & CORNER TEARS
7. RAPESEED SCABS
8. CORNER BLEEDER
9. BROADFACE BLEEDER
10. COLLAR
11. ROLL/GUIDE MARKS
12. UNDERFILL

PLANT NAME:           HEAT NUMBER:
DATE:                 CUT NUMBER:
TIME:                 DISPOSITION:

IMPERFECTION A              IMPERFECTION B
TYPE:                       TYPE:
START COORDINATES:          START COORDINATES:
END COORDINATES:            END COORDINATES:
IMPERFECTION SIZE:          IMPERFECTION SIZE:

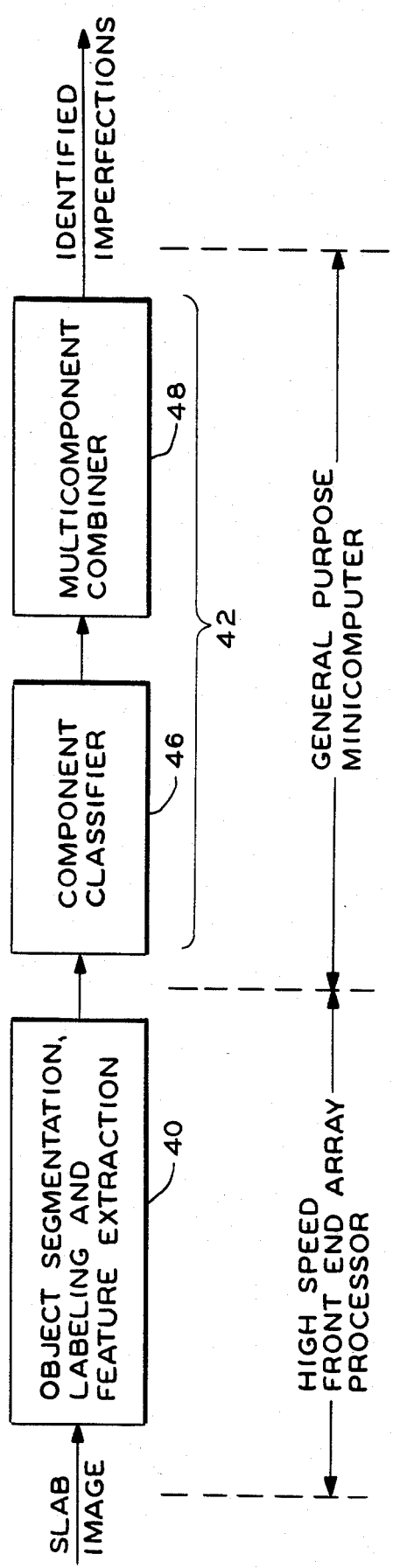
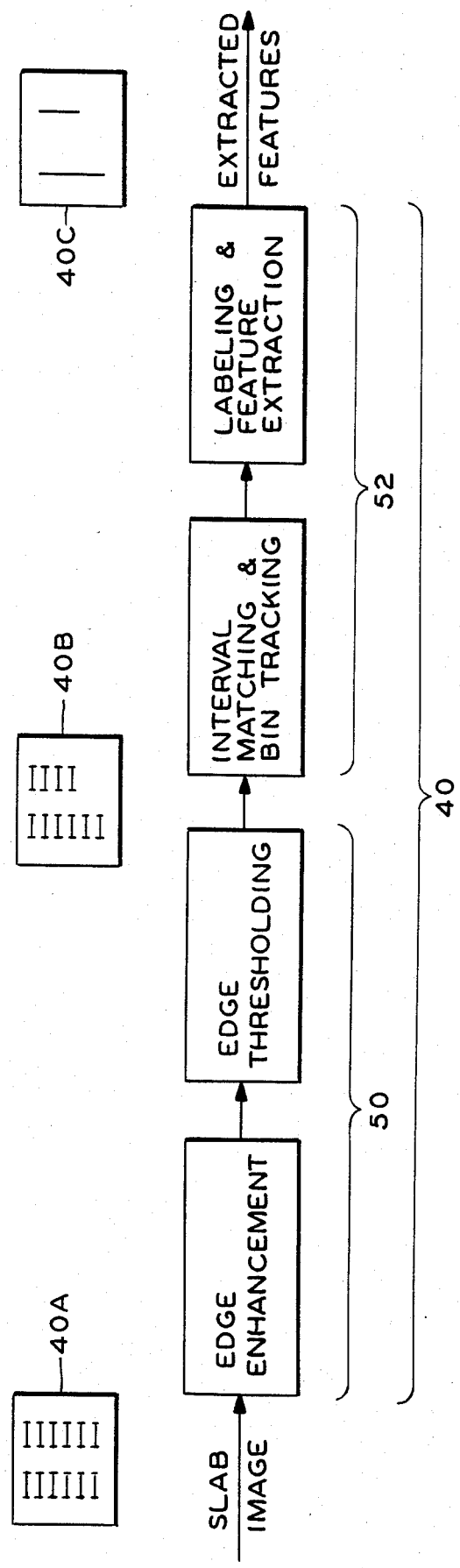
FIG. 5
FIG. 6

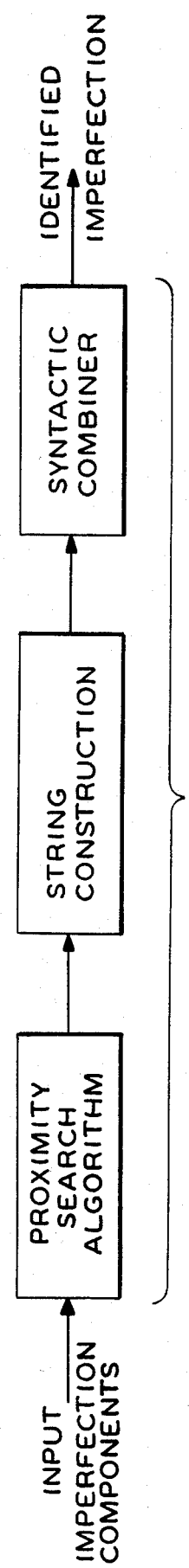
FIG. 9
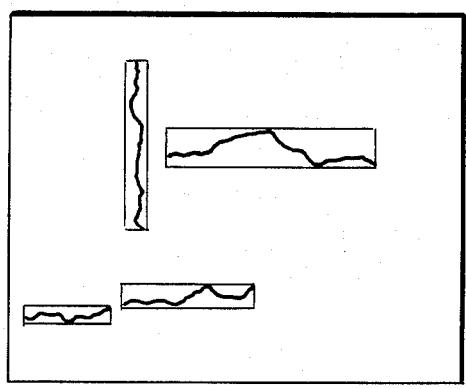
FIG. 10
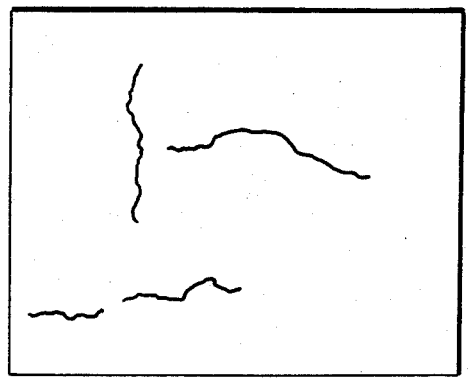

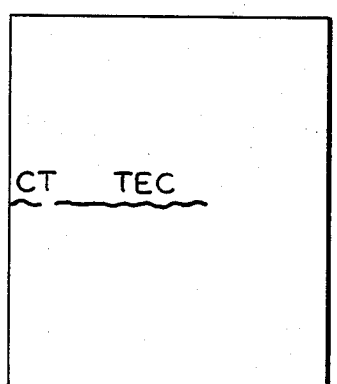
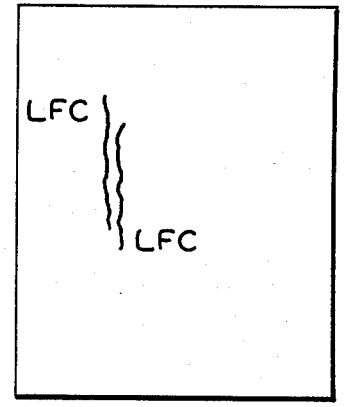
CT − TFC → TFC   LFC + LFC → LFC
EACH FILE OF CONNECTED STRINGS IS CONNECTED PAIRWISE UNTIL THE STRING IS REDUCED TO A SINGLE IMPERFECTION
FIG. 11
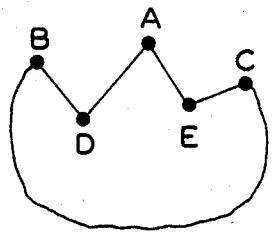
FIG. 12
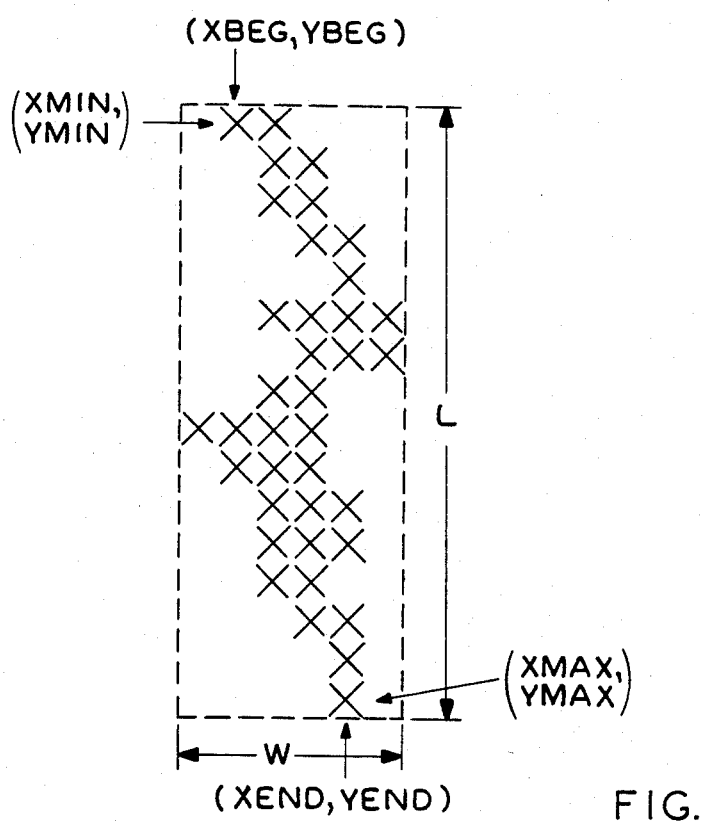
FEATURES:
PA = 37
L = 16
W = 6
LGL = 29
RGL = 24
S = 2.67
F = .385
AGL = 26.5
CR = .188
FIG. 13

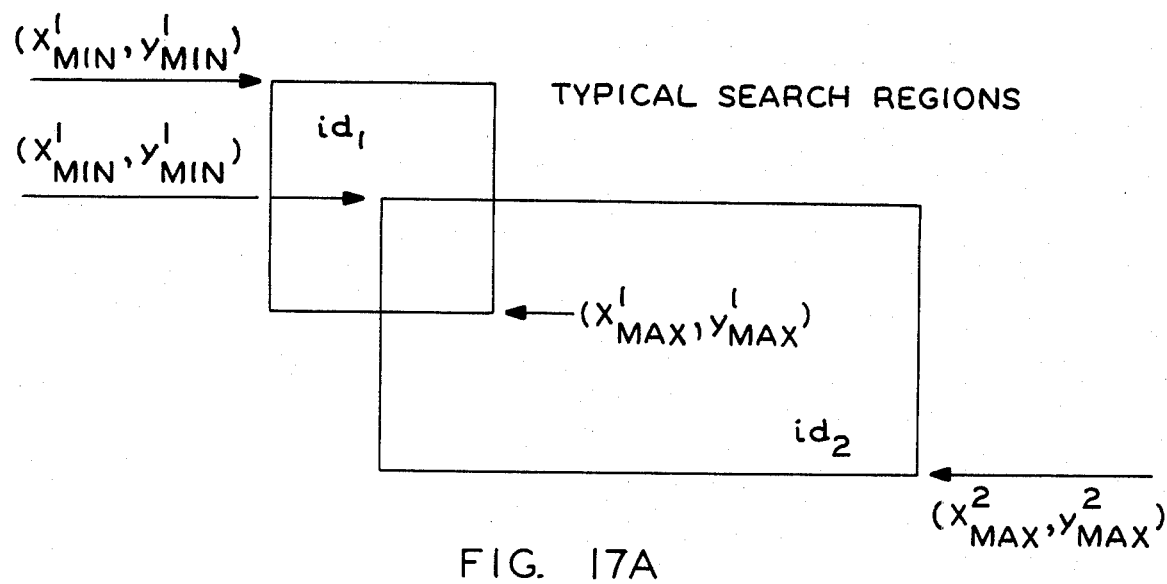
FIG. 17A
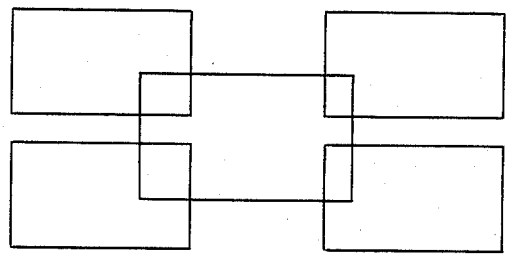
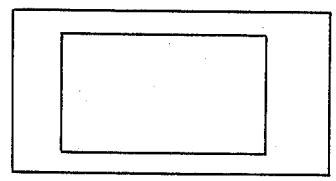
FIG. 17B

LONGITUDINAL CASE
(XEND,YEND)
(XBEG,YBEG)    DISTANCE THRESHOLDED
TRANSVERSE CASE
XMIN1    XMAX1  XMIN2    XMAX2
         XMIN2 - XMAX1
    XMAX2 - XMIN1
FOR THE CASE PICTURED:
  DISTANCE THRESHOLDED = MIN (ABS(XMAX1-XMIN2),
                               ABS(XMAX2-XMIN1))
                       = XMIN2 - XMAX1
FIG. 20
IMPERFECTIONS WITH CIRCUMSCRIBING RECTANGLES:
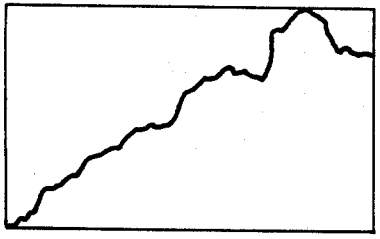
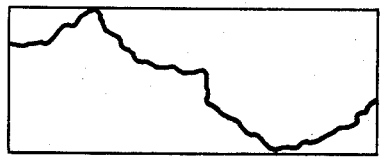
IMPERFECTION SLANTS:
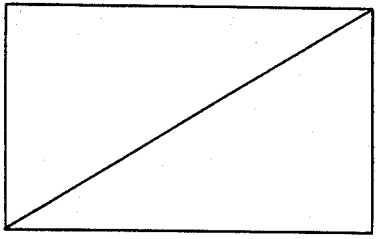
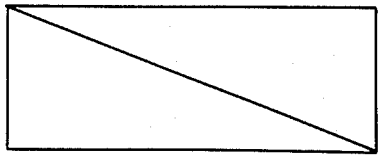
FIG. 21

INPUT:

OUTPUT:

TFC, IF NOT FULL SLAB WIDTH

OR

DP, IF FULL SLAB WIDTH

TABLE VI  PHYSICAL ATTRIBUTES

| IMPERFECTION | LENGTH | WIDTH | DEPTH |
|---|---|---|---|
| LFC | L | AW | 1.3*AW |
| LCC | L | AW | 1.3*AW |
| CM | L | AW | 1.3*AW |
| CT | W | AL | 2.0*AL |
| TFC | W | AL | 3.3*AL |
| DP | W | AL | 3.3*AL |
| RS | MAX (L,W) | MIN (L,W) | 0.125 |
| SPT | MAX (L,W) | MIN (L,W) | 4.0*MIN 0.125 |
| BB | MAX (L,W) | PA/MAX (L,W) | 3.3*MAX(L,W) |
| CB | L | AW | 1.3*AW |

FIG. 23

TABLE VIIa  MERGED PHYSICAL ATTRIBUTES: END TO END

| IMPERFECTION | LENGTH | WIDTH | DEPTH |
|---|---|---|---|
| LFC | $\sum L_i$ | MAX ($AW_i$) | MAX ($D_i$) |
| LCC | $\sum L_i$ | MAX ($AW_i$) | MAX ($D_i$) |
| CM | $\sum L_i$ | MAX ($AW_i$) | MAX ($D_i$) |
| CT | $\sum W_i$ | MAX ($AL_i$) | MAX ($D_i$) |
| TFC | $\sum W_i$ | MAX ($AL_i$) | MAX ($D_i$) |
| DP | $\sum W_i$ | MAX ($AL_i$) | MAX ($D_i$) |
| RS | N/A | N/A | N/A |
| SPT | N/A | N/A | N/A |
| BB | N/A | N/A | N/A |
| CB | N/A | N/A | N/A |

FIG. 24A

TABLE VIIb MERGED PHYSICAL ATTRIBUTES: OVERLAPPING AND PARALLEL

| IMPERFECTION | LENGTH | WIDTH | DEPTH |
|---|---|---|---|
| LFC | MAX ($L_i$) | $\sum PA_i / MIN (L_i)$ | 1.3 (MERGED WIDTH) |
| LCC | MAX ($L_i$) | $\sum PA_i / MIN (L_i)$ | 1.3 (MERGED WIDTH) |
| CM | MAX ($L_i$) | $\sum PA_i / MIN (L_i)$ | 1.3 (MERGED WIDTH) |
| CT | MAX ($W_i$) | $\sum PA_i / MIN (W_i)$ | 2.0 (MERGED LENGTH) |
| TFC | MAX ($W_i$) | $\sum PA_i / MIN (W_i)$ | 3.3 (MERGED LENGTH) |
| DP | MAX ($W_i$) | $\sum PA_i / MIN (W_i)$ | 3.3 (MERGED LENGTH) |
| RS | N/A | N/A | N/A |
| SPT | N/A | N/A | N/A |
| BB | N/A | N/A | N/A |
| CB | N/A | N/A | N/A |

FIG. 24B

TABLE VIIIa SLAB DISPOSITION: SHEET

| IMPERFECTION | DIRECT SHIP | CONDITION | SIDETRIM | SIDETRIM OR BURNBACK | DISTRESS SALVAGE | BURNBACK OR SCRAP |
|---|---|---|---|---|---|---|
| LFC | NONE ALLOWED | D<.375 | | | .375≤D≤.75 | D>.75 |
| LCC | D≤.375 | .375<D<.25 | D≥.75 | | | |
| CM | | | ALL | | | |
| CT | D≤.5 & L≤1.0 | .5<D<.75 1.0<L≤3.0 D≥.5 L≤1.0 | | D≥.75 & L>3.0 | | |
| TFC | NONE ALLOWED | D<.375 | | | | D≥.375 |
| DP | | | | ALL | | |
| RS | NONE ALLOWED | ALL OCCUR- ENCES | | | | |
| SPT | D<.125 | .125≤D & L≤3.0 | | D≥.75 & L>3.0 | | |
| BB | NONE ALLOWED | D<.375 | | | .375≤D≤.5 | D>.5 |
| CB | D≤.375 | .375<D<.75 | D≥.75 | | | |

FIG. 25A

TABLE VIIIb SLAB DISPOSITION: TIN MILL

| IMPERFECTION | DIRECT SHIP | CONDITION | SIDETRIM | SIDETRIM OR BURNBACK | DISTRESS SALVAGE | BURNBACK OR SCRAP |
|---|---|---|---|---|---|---|
| LFC | NONE ALLOWED | D<.375 | | | .375≤D≤.75 | D>.75 |
| LCC | NONE ALLOWED | D<.75 | D≥.75 | | | |
| CM | | | ALL | | | |
| CT | NONE ALLOWED | D<.75 & L≤3.0 | | | | |
| TFC | NONE ALLOWED | D<.375 | | | | D≥.375 |
| DP | | | | ALL | | |
| RS | W<.5 & L<.5 | W≥.5 OR L≥2.25 | | | | |
| SPT | D<.125 | D≥.125 & L≤3.0 | | D≥.75 | | |
| BB | NONE ALLOWED | D<.375 | | | .375≤D≤.5 | D>.5 |
| CB | NONE ALLOWED | D<.75 | D≥.75 | | | |

FIG. 25B

TABLE VIIIc SLAB DISPOSITION: D&I

| IMPERFECTION | DIRECT SHIP | CONDITION | SIDETRIM | SIDETRIM OR BURNBACK | DISTRESS SALVAGE | BURNBACK OR SCRAP |
|---|---|---|---|---|---|---|
| LFC | NONE ALLOWED | D<.375 | | | $.375 \leq D \leq .75$ | D>.75 |
| LCC | NONE ALLOWED | D<.75 | $D \geq .75$ | | | |
| CM | | | ALL | | | |
| CT | NONE ALLOWED | D<.75 & L≤.30 | | $D \geq .75$ | | $D \geq .375$ |
| TFC | NONE ALLOWED | D<.375 | | ALL | | |
| DP | | | | | | |
| RS | W<.5 & L<.25 | W≥.5 OR L≥.25 | | $D \geq .75$ | | |
| SPT | D<.125 | .125≤D & L≤3.0 | | | | |
| BB | NONE ALLOWED | D<.375 | | | $.375 \leq D \leq .5$ | D>.5 |
| CB | NONE ALLOWED | D<.75 | $D \geq .75$ | | | |

FIG. 25C

REAL TIME AUTOMATED INSPECTION

The Government has certain rights in this invention pursuant to Contract No. DE-FC07-79CS-40242 awarded by the Department of Energy.

The invention relates to a real-time automated system for detecting and classifying surface defects of hot steel slabs and producing outputs identifying and mapping the locations of the defects.

The American steel industry is one of the largest consumers of energy in the United States. A significant amount of this energy is spent in the heating and cooling of steel. In recent years the trend in steelmaking technology in the United States has been increasingly shifting towards the continuous casting of steel. This trend is also evident in Japan, Germany, France and Sweden.

In a continuous caster, molten steel is continuously poured into a mold which is water cooled. The steel, as it solidifies, is drawn out of the mold in a perpetual ribbon along a roll table. This ribbon is then cut off at predetermined lengths to form steel slabs. Unfortunately, the steel slabs often have surface imperfections which must be detected and, depending on their severity, must be conditioned before further processing of the steel slab.

Currently in most steel mills, the hot slab coming out of a caster is cooled to the ambient temperature. An inspector then gets down on hands and knees on the slab to manually detect surface imperfections. If a slab is determined to be free of imperfections, it has to be heated again for further processing in a hot strip rolling mill.

An automated inspection system in accordance with the present invention is capable of inspecting a slab coming out of a caster while it is still hot. If a slab is found to be free of imperfections, it can be shipped directly for in-line rolling. This thus permits avoiding the intermediate cooling and reheating processes currently necessary for manual inspection and the wasting of energy associated therewith.

Steel slabs produced in a continuous caster are susceptible to a wide variety of surface imperfections. A listing and illustration of these imperfections is referred to further on herein. The ultimate disposition of a slab depends upon the number and identity of these imperfections as well as their severity.

The concept of the automatic inspection system of the present invention involves a data camera which views the slab in the transverse direction. As the slab moves under its field of view, the data camera scans the slab in contiguous lines thus generating the slab image. A position camera is used to view the slab in the longitudinal direction, thus enabling the determination of the slab position. Solid state linear array cameras with 2048 picture sensing elements may be used for data collection as well as position sensing. The slab imagery is first compensated for gain and bias non-uniformities in the sensor. The converted data is then routed via the interface electronics to processing equipment for image processing and classification. The processing equipment comprises an array processor and a host minicomputer.

In addition to detecting and identifying surface imperfections the system also determines the location on the slab of the imperfections and their physical parameters such as length, width and area, etc. Once these have been determined, the slab disposition, such as direct ship for rolling, further conditioning or scrap can be automatically determined from the quality control criteria prevalent in the steel mill.

In a particular embodiment of the invention the requirements of the inspection system translated to a data throughput rate on the order of 500K pixels/sec. The inspection system operates in real time and generates a report for each slab inspected. A typical slab report comprises a pictorial display of the slab along with a map of the imperfections. The report also includes a transcription for each detected imperfection which includes its identity, i.e., imperfection class, location and size.

The essence of real-time processing is the selection and design of algorithms and hardware which can process data as fast as it arrives. All the processing of an individual pixel need not be done before the successive pixel arrives. By staging operations and adding more processing power to the system, the desired throughput can be maintained, so long as the processing time per pixel of each stage is less than the interarrival time. This establishes a tradeoff between speed and the cost of the system.

The real-time processing requirement of the inspection system is accomplished herein with special processing architecture and a unique set of algorithms for processing the data. In the image processing part of the inspection system the incoming slab image is first processed by a high speed front end consisting of the array processor which peforms object segmentation as well as feature extraction. The segmented object features are passed to the host minicomputer which performs classification of the imperfections in a two-step process. Each incoming object, termed as a component, is first classified based on its features in a component classifier. These components are then examined by a multi-component combiner which uses syntatic/semantic rules to determine if any of the identified objects are fragmented components of a larger imperfection. If so, these components are combined to form the single, larger imperfection and assigned to an appropriate class. The identified imperfections are then consolidated into a slab imperfection report by the minicomputer.

The extremely high throughput of this system would make it difficult or impractical to join the components during the segmentation stage by using line enhancement techniques such as relaxation labeling because most line enhancement techniques require a premium in terms of processing time. Rather the approach herein is to use a hierarchic statistical classifier for identifying the individual components and use syntactic rules for piecing together the individual components.

A main object of the invention is to provide a new and improved real-time automated system for the inspection of hot steel slabs.

Other objects of the invention will become apparent from the following specification, drawings and appended claims.

In the drawings:

FIG. 5 is a block diagram which illustrates the functions of the high speed front end array processor and the minicomputer which comprise the digital processing equipment;

FIG. 6 is a block diagram which illustrates the specific functions of the array processor;

FIG. 9 is a block diagram of the multicomponent classifier shown in FIG. 5.

FIG. 10 is an illustration of the proximity search algorithm performed by the multicomponent classifier;

FIG. 11 shows examples of end-to-end and side-by-side components which would be considered for combining in the multicomponent classifier shown in FIGS. 5 and 9.

FIG. 12 is similar in principle to FIG. 7;

FIG. 13 represents an example of a tracked imperfection object with associated features being indicated;

FIGS. 17A and 17B illustrate search regions for a multi-component classifier analysis;

FIG. 20 illustrates the utilization of a string construction in connection with determining end-to-end crack conditions;

FIG. 21 illustrates the utilization of a string construction in connection with determining parallelism relative to crack conditions;

FIG. 23 is a table which lists the physical attributes of slab surface imperfections;

Figure 2:
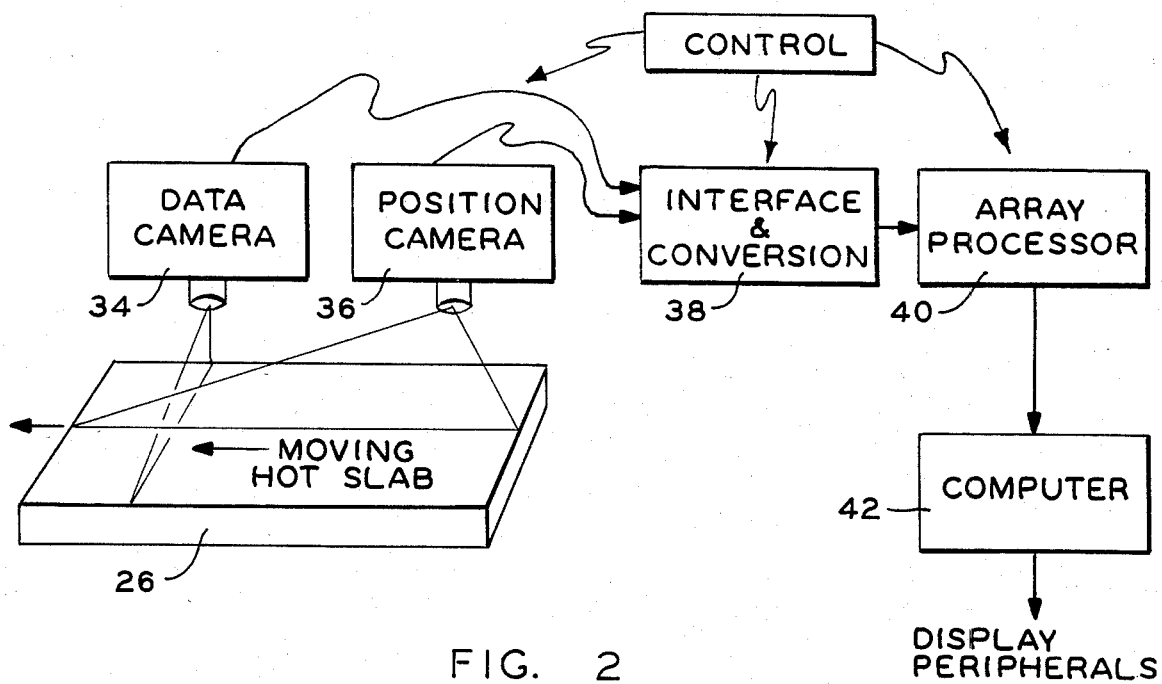
FIG. 2 is a block diagram of a general overview of the automatic inspection system.
Figure 26:
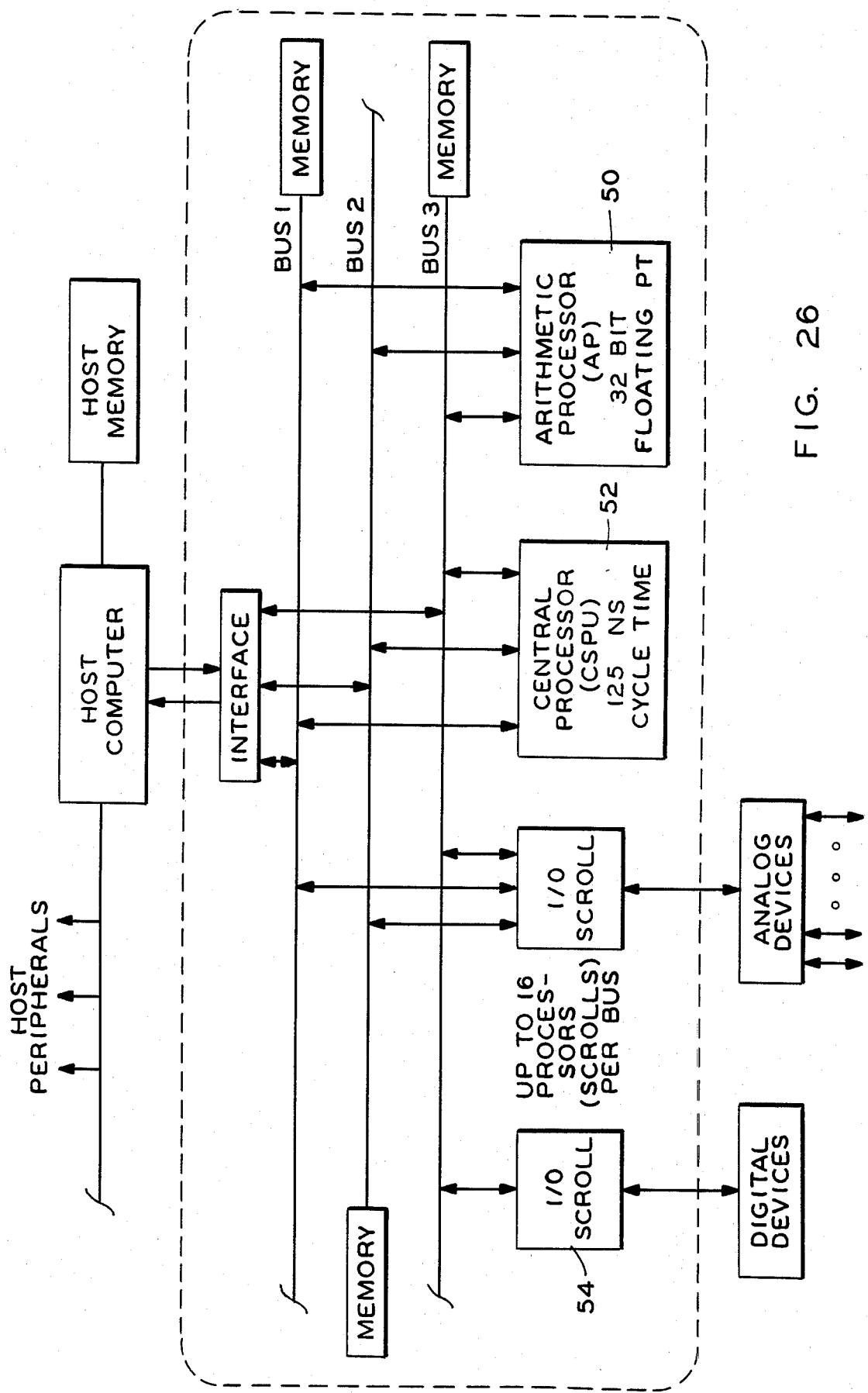
Figure 27A:

FIGS. 24A and B are tables which list merged physical attributes of slab surface imperfections;

FIGS. 25A, B and C are tables which list slab disposition decisions based on summarized output information;

FIG. 26 is a block diagram of the hardware of the array processor shown variously in FIGS. 2, 5 and 6; and FIGS. 27A, B, C and D illustrate the results of a logarithmic companding operation.

Figure 1:
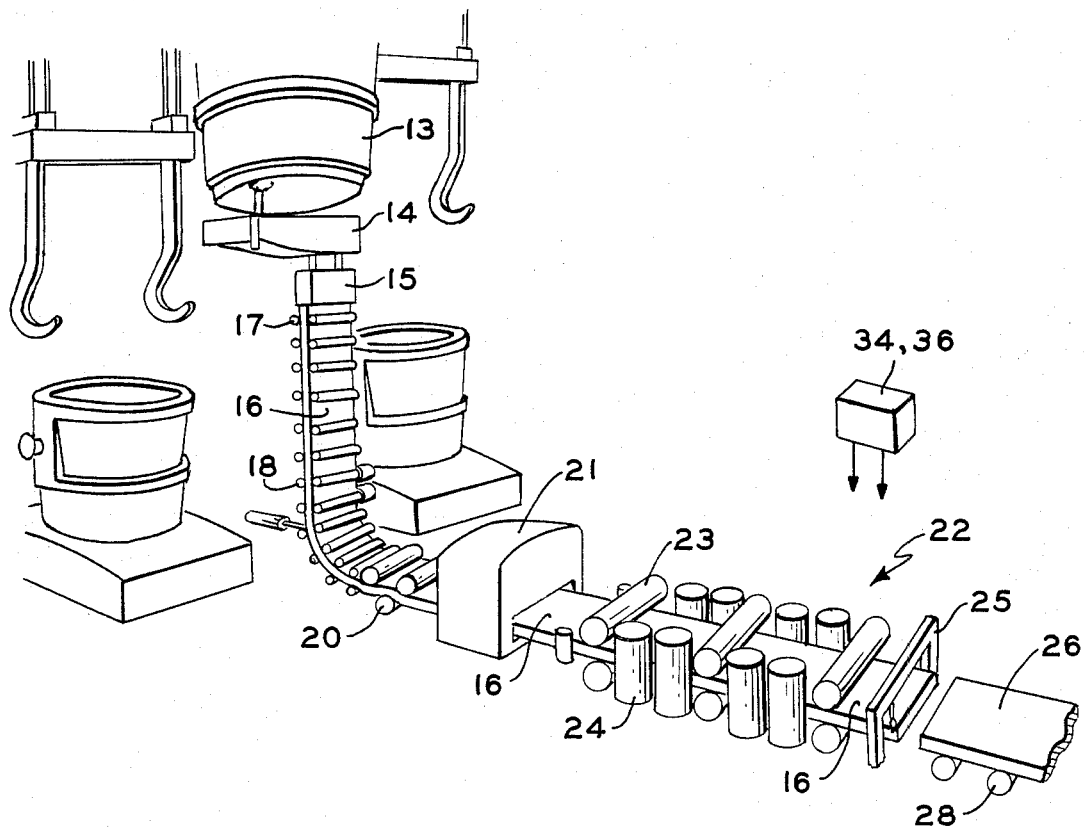
FIG. 1 is a perspective overall view of a steel mill installation of a continuous slab caster of the type which produces slabs which may be automatically inspected for surface defects by a process embodying the invention herein disclosed.

Referring to FIG. 1, there is shown a steel mill installation of a continuous slab caster comprising a ladle 13 for supplying molten steel to a tundish unit 14 which directs molten steel to a flow through mold 15. Mold 15 discharges a semi-molten ribbon of steel 16 from the bottom thereof which descends vertically between sets of guide rolls 17 and pinch rolls 18.

Near the floor level is a set of straightener rolls 20 which direct the ribbon of steel horizontally through a furnace 21 to a sizing mill 22. Sizing mill 22 comprises sets of horizontally and vertically aligned rollers 23 and 24 which reduce the cross sectional area of the ribbon of steel to predetermined desired dimensions. Following the sizing mill is a cutting torch unit 25 which cuts the moving ribbon of steel at desired intervals to obtain steel slabs 26 of desired lengths. Following the cutting torch unit is a roll table 28 upon which the slab 26 moves in transit to a staging area (not shown) which is referred to below.

Two linear scanning array data and position cameras 34 and 36 may be positioned ten to fifteen feet above the cutting torch unit 25 from which positions a section of the ribbon of steel 16 just ahead of the cutting torch unit can be scanned. The cameras comprise the sensing aspect of the system.

The term "slab" is used herein and in the claims refers interchangeably, i.e., without distinction, to either a cut-off, articulated slab as indicated by the numeral 26 or a portion of the ribbon 16 ahead of the cutting torch unit 26 having a predetermined length. Whether or not the "slab" is ahead of or downstream from the cutting torch unit 16 is thus not material with regard to the scope of the invention.

In the steel industry a steel slab such as the slab 26 is a rectangular piece of steel that is usually 3 to 12 inches thick, 24 to 84 inches wide and over 10 feet long. Slabs produced at U.S. Steel (Gary and Homestead Works) are 3 to 23 inches thick, 22 to 76 inches wide and 4 to 40 feet long.

An automated inspection system must be capable of inspecting the slabs while they are hot and while in motion at speeds up to 320 inches per minute. The slab might have movement from side to side a distance of ±6 inches on the roll tables and in such case, assuming a 76 inch wide slab by way of example, the system would have to have the capability to acquire image data over an 88-inch field of view to cover the 76-inch wide slab in its extreme positions. Further, the system must be able to compensate for variations in height due to slab thickness (up to 18 inches) and slab flatness variations after shearing (approximately 18 inches). The system is capable of acquiring real time data from a moving slab of steel with sufficient resolution to detect surface imperfections measuring 0.03 inch wide.

A general overview of the automatic inspection system is shown in FIG. 2.

Data camera 34 views the slab in the transverse direction. As the slab moves under its field of view, the data camera scans it in contiguous lines thus generating a sampled analog image of the slab surface. Position camera 36 is used to view the slab in the longitudinal direction, thus enabling the determination of the slab position and velocity to provide control for the transverse scans of data camera 34. Fairchild solid state linear array cameras with 2048 picture sensing elements may be used for data collection as well as the position sensing. The slab surface imagery is first compensated for gain and bias non-uniformities in the sensor. The converted data is then transmitted in real time via an interface 38 to digital processing equipment for image processing and pattern recognition of surface defects. Such equipment comprising an array processor 40 and a host minicomputer 42.

The transverse line scans of camera 34 present a high resolution TV-like image which is analyzed by high speed data processing utilizing the array processor 40 and the minicomputer 42. A succession of scans provides images on which image recognition algorithms operate and the results are then printed out on appropriate displays containing slab identification, anomaly code and position information.

Of importance in the concept of the invention are the speed of inspection and the development of the algorithms for the recognition, categorization and disposition of imperfections.

Steel slabs to which the invention is directed may come from at least two sources which are (1) continuous-slab casters as illustrated in FIG. 1 and (2) primary-mill rolling (not illustrated) of ingot-cast steel.

Steel slabs that emerge from a slabbing mill or a continuous caster have average temperatures in the range of 1500° to 2100° F. A preferred imaging technique utilizes mercury lamps to illuminate the slab, with the reflected light being used to image the slab.

Figure 3:
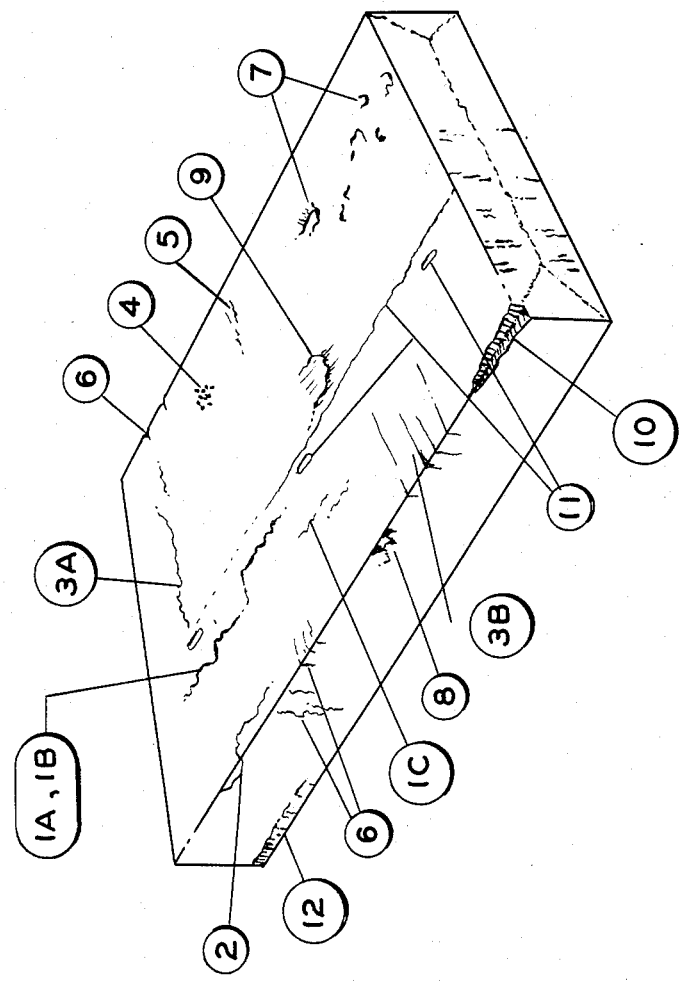
FIG. 3 is a perspective view of a slab upon which is illustrated the various types of imperfections that occur on a slab of a continuous caster type unit.

Steel slabs produced in a continuous caster may have a wide variety of surface imperfections. FIG. 3 is a perspective view of a slab upon which is illustrated the various types of imperfections that occur on a slab of a continuous caster type unit. In general, cracks appear darker than their surrounding areas, due to their shadows.

The ultimate disposition of a slab 26 depends upon the number and identity of those imperfections as well as their severity. In addition to detecting and identifying surface imperfections, the system also determines the location on the slab of the imperfections and their physical parameters such as length, width, area, etc. Once these have been determined the slab disposition, such as direct ship for rolling, condition further, or scrap, may be automatically determined from the quality control criteria prevalent in the steel mill.

For the sake of simplicity the disclosure herein refers specifically to only the upper surface of the slab. It is apparent, however, that imperfections in the side and bottom surfaces of the slab will also have a bearing on the disposition of a slab. In an actual installation additional cameras and other related processing equipment will thus be required for detecting and evaluating the imperfections of these other surfaces. Such additional equipment only parallels the disclosed equipment and a disclosure thereof would not add any substance to the disclosure herein.

Figure 4:
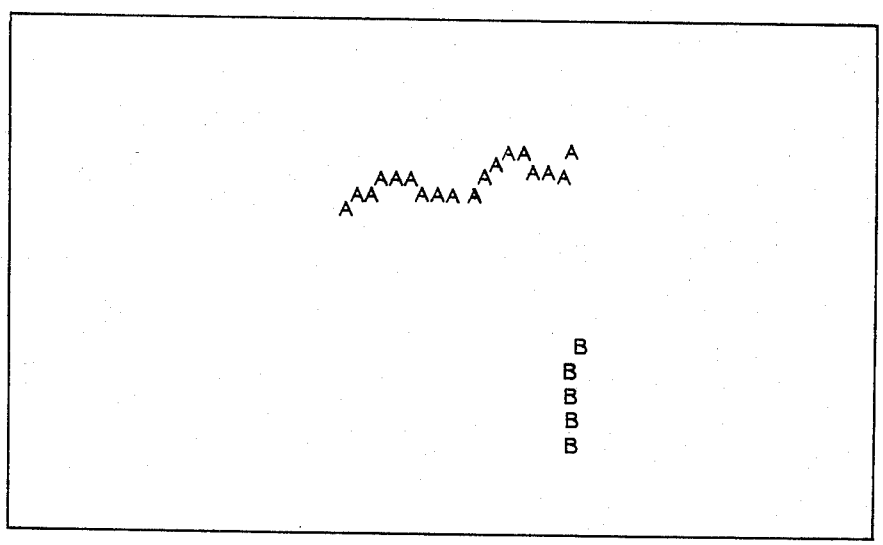
FIG. 4 is a sample report form which comprises a pictorial display of a slab along with a map of the imperfections and a reference to the data to be output.

A data throughput rate for the upper slab surface of a test installation was 546K pixels/sec. The inspection system operates in real time and generates a report for each slab inspected such as the report shown in FIG. 4. The report consists of a pictorial display of the slab along with a map of the imperfections. The report also includes a transcription for each detected imperfection which includes its identity (i.e., imperfection class), location and size as indicated in FIG. 4.

The real-time processing requirement of the inspection system has necessitated a special processing architecture and a unique set of algorithms for processing the data. The image processing system of the inspection system is shown in FIG. 5. The incoming slab imagery is first processed by a high speed front end unit consisting of the array processor 40 which performs object segmentation as well as feature extraction. The segmented object features are passed to the host minicomputer 42 which performs classification of the imperfections in a two-step process as shown in FIG. 5. Each incoming object, termed as a component, is first classified based on its features in a component classifier 46. These components are then examined by a multicomponent combiner 48 which uses syntactic/semantic rules to determine if any of the identified objects are fragmented components of a larger imperfection. If so, these components are combined to form a single, larger imperfection and assigned to an appropriate class. The identified imperfections are then consolidated into a slab imperfection report as shown in FIG. 4 by the minicomputer 42.

This completes a general overview of the system. The image processing algorithms are described hereinafter, first in general terms and then in some detail.

Referring to the algorithms, the edge segmentation approach is utilized because most of the slab imperfections manifest themselves as linear discontinuities in a uniform background. The object segmentation algorithms are performed by the array processor 40. FIG. 6 shows the sequence of the object segmentation, labeling and feature extraction operations as they are implemented in the array processor 40. The array processor consists of two processing units called the Arithmetic Processing Unit 50 (APU) and a Central Signal Processing Unit 52 (CSPU). The operations performed by the APU and the CSPU are indicated in FIG. 6.

The incoming image 40A is first processed by an edge enhancement operator. The Roberts Gradient operator was chosen for its performance and low computational overhead. The edge enhancement operation is done on the fly on a scan-line basis using only the adjacent scan lines required by the Roberts Gradient operator.

The edge enhanced image is then thresholded to segment out the object edges as indicated in 40B. The selection of a proper threshold is crucial in order to cut down on clutter while retaining the primary objects of interest. In examining the slab imagery, it was discovered that the slab surface could be divided into three homogeneous zones based on the imagery statistics. These three distinct zones come about because of the peculiar geometry of the rollers in a steel mill caster. However, within a given zone, the image statistics were observed to be fairly stationary.

Accordingly, a different thresholding scheme was used for each zone. Fixed thresholds were used for the first two zones, with a different threshold being used for each zone. However, an adaptive threshold was found to be necessary for the third zone in order to provide an acceptable level of performance. A recursive filter is used to obtain a smoothed sum of the enhanced edges with an appropriate time constant. This smoothed sum is multiplied by a fixed constant in order to provide a continuously adaptive segmentation threshold.

After the thresholding operation, each scan line of the image 40B will only contain segments of the image which correspond to the edges of the objects of interest, i.e., the slab imperfections. These segments are referred to as intervals on any scan line of the image. The approach herein to establishing connectivity between intervals that constitute the same object consists of conducting a sequence of spatial overlap checks. These overlap checks are referred to as "interval matching and bin tracking" operations for reasons that will be apparent.

Figure 7:
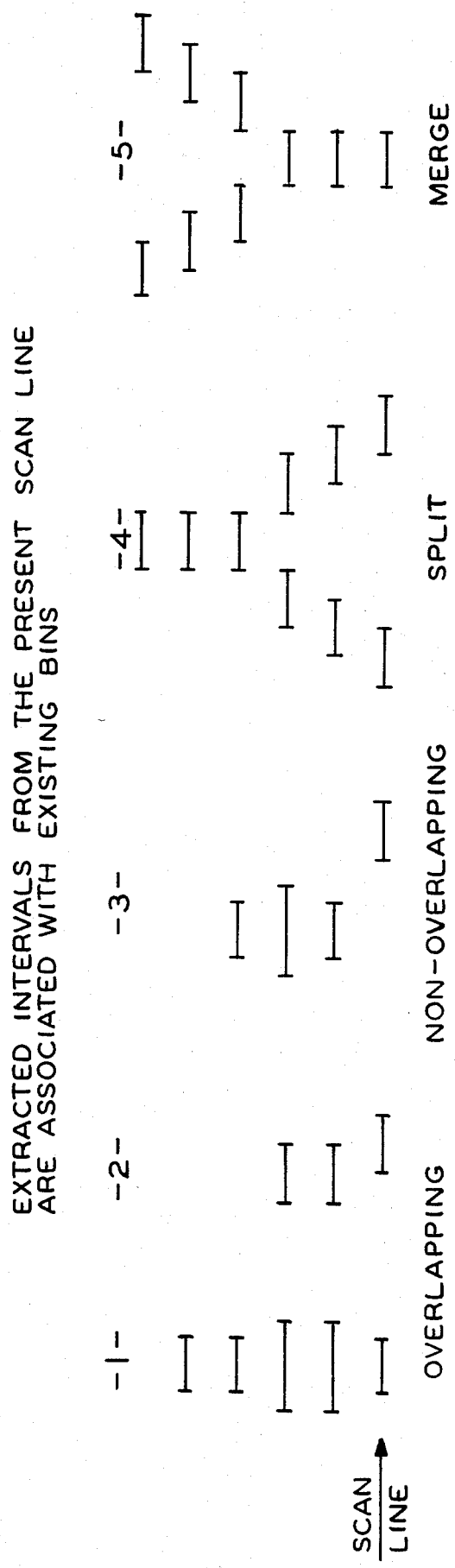
FIG. 7 is a schematic showing the presence or absence of connectivity between intervals on a scan line and object established on preceding scan lines.

On the first scan line of the image, each interval is assigned to a bin. On subsequent scan lines, each of the incoming intervals is examined to see if it matches any of the existing bins, i.e., if it spatially overlaps any of the bins. The first two instances in FIG. 7 illustrate cases where the intervals match existing bins. When such an interval match occurs, the previously existing bin is extended to the current scan line. The bins, each of which represents an object, are thus tracked from scan line to scan line. However, when an interval does not match any of the existing bins, the interval is used to start a new bin and thus a new object is born. The third instance in FIG. 7 shows the case of an interval wich does not overlap the pre-existing bin. The fourth and fifth instances of FIG. 7 illustrate splitting and merging of bins.

In actuality the bin tracking is done in a more complex way then indicated above. This complexity is necessitated by the numerous special cases which arise due to noise, poor contrast in the image, etc. A more detailed exposition of these subtleties appears further on herein.

Objects are labeled (40C of FIG. 6) by assigning a unique identifier to each bin tracked. The geometrical features of the object, such as length, width, area, etc. are also implicitly accrued during the bin tracking operation. The dissociation of the bin tracking and feature extraction operation as shown in FIG. 6 is artificial and has only been done to illustrate the logical flow of operations.

The segmented objects along with their features are transmitted to the minicomputer 42 for classification. Each of the segmented objects is classified in a two stage process as indicated in FIG. 5. In the first stage each object is assigned a tentative class in the component or object classifier 46. This is done because each incoming object is suspected of being a potentially fragmented component of a larger object. The choice of the term "component classifier" is thus evident.

The rationale for the classifier design and the various thresholds can be explained quite simply. As explained before, after segmentation in the environment of the array processor 40, imperfections are represented by feature vectors. A feature vector is a list of numbers which indicates the location and geometry of the imperfection. In the component classifier 46, threshold values are utilized as bounds on these numbers to group imperfections into descriptive classes such as "longitudinal crack close to the edge of the slab", which denotes a longitudinal corner crack.

For instance, if XMAX is a feature vector coordinate indicating maximum distance of an imperfection from the edge of the slab, and T is a small (threshold) value, then the statement "XMAX<T" may be interpreted as "imperfection is close to the edge of the slab". Such a threshold T would be picked based on steel mill specifications.

As another example, consider the ratio of maximum length to maximum width (L/W) of an imperfection. Thresholding this feature indicates how much longer or shorter an imperfection is, that it is wide. "L/W>T" means that the imperfection is more than T times longer than it is wide. This information is useful in determining the general orientation of an imperfection. All the node classifiers of the component classifier 46 have been designed using criteria and thresholds such as these.

Figure 8:
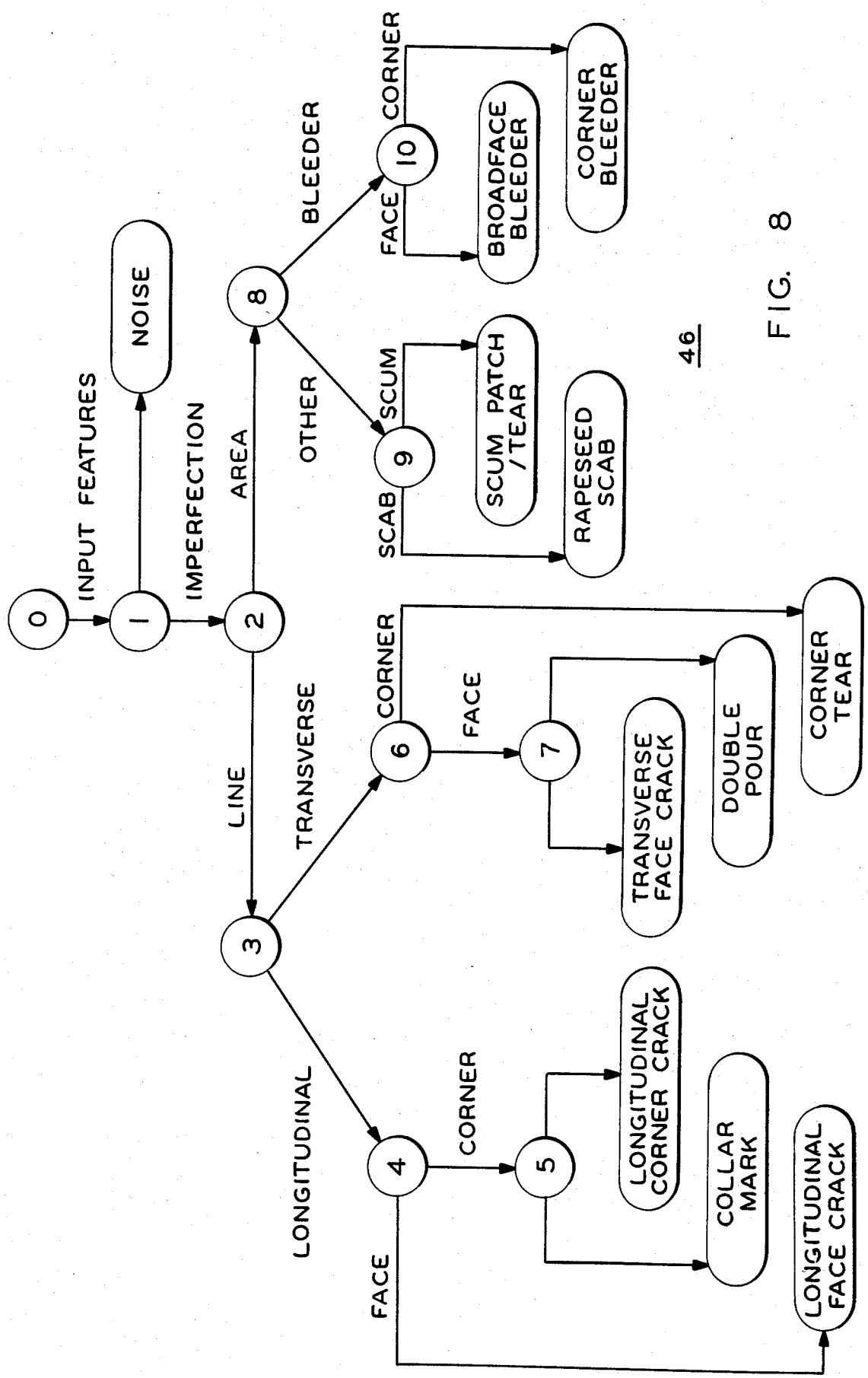
FIG. 8 illustrates a component classifier as being implemented by a hierarchial tree flow chart.

The component classifier 46 is implemented as a hierarchial tree classifier as shown in FIG. 8. Each object to be classified trickles through a series of node classifiers which successively narrow the list of possible classes for the object until it is finally classified. Each node classifier is a binary statistical classifier which makes a series of logical checks on the object features.

As an aid in understanding the component classifier 46, the path of a hypothetical imperfection, for example, a Longitudinal Face Crack (LFC), is traced. Node classifier 1 checks the object area to see if it is large enough to be an imperfection or if it is a noise object. Node classifier 2 then checks if the object is a line imperfection (crack, tear) or an area imperfection (pit, patch); the former, in this case. Node classifier 3 checks the orientation of the object and ascertains that it is longitudinal. Finally, Node classifier 4 checks the location of the object and finds that it is located on the broadface of the slab, away from the slab corner. Thus the imperfection is classified as a Longitudinal Face Crack.

Once all the segmented objects on a slab have been classified by the component classifier 46, they are examined in the Multicomponent Combiner (MCC) 48. If any of the objects are found to be fragmented components of a larger object, they are combined and the larger object is assigned an appropriate class. Objects that don't need to be combined are retained as they are.

A block diagram of the MCC 48 is shown in FIG. 9. The components are first processed by a proximity search algorithm to see if any of the components are located physically "close" to one another. Proximity is a necessary condition for two components to be combined into one. The spatial relationships of the proximate components are then determined and a string of objects that are potentially connectable is constructed. A certain spatial relationship is once again a prerequisite for two components to be combined. Finally syntactic/semantic rules are applied to each string to combine all the components in that string and assign it to an appropriate class. Each of these steps is detailed in the following paragraphs.

The proximity search algorithm is illustrated in FIG. 10. Shown on the left side are four components identified on a slab. The search is started by defining the minimum bounding rectangle around each component. Each rectangle is then augmented by a certain amount, in effect defining a bubble around each component. Obviously, two components are proximate if their bubbles touch. A fast, modified sorting algorithm is then used to construct files of proximate components. For the example of FIG. 10, the proximity search algorithm would output two files, with each file containing two proximate components. Each file of proximate components is then examined to see if the components bear one of two possible spatial relationships. The two spatial relationships of interest are the "end-to-end" condition (denoted by the symbol "−") and the overlapping and parallel condition (denoted by the symbol "+").

The end-to-end condition usually prevails when an imperfection is broken in the middle due to improper segmentation. The first illustration in FIG. 11 shows an example where a single crack is broken into two components which are identified by the component classifier 46 as a Corner Tear (CT) and a Transverse Face Crack (TFC) respectively. Since the two are aligned end-to-end, a string may be constructed as CT−TFC, thus explicitly displaying their spatial relationship.

The overlapping and parallel condition occurs most commonly when the two edges of a wide crack on the slab are segmented as two components. The parallelism referred to is to be interpreted liberally and is not meant to convey geometric parallelism.

The second illustration in FIG. 11 shows a wide crack where each component thereof has been classified as a Longitudinal Face Crack (LFC) by component classifier 46. As the two are parallel and overlap spatially, a string is constructed out of them as LFC+LFC, conveying their spatial relationship.

In this manner a string is constructed out of each file of proximate components. It is worth noting that two proximate components in a file will not be written out into a string unless one of the two aforementioned spatial relationships prevails.

The last step that remains is to combine the components in each string and assign an appropriate class to the single large imperfection using predetermined syntactic rules. In the first example in FIG. 11, the two imperfections are combined to form a single transverse face crack. In the second example, the components are combined to form a single longitudinal face crack.

The slab inspection is now complete and the minicomputer 42 prepares a slab report as described above.

Detailed descriptions of the algorithms utilized are as follows:

ALGORITHMS

The overall inspection algorithm for the hot steel slabs which has been referred to above and which is described in more detail hereinafter has the following major constituents:

Logarithmic Companding of Intensity Data
Edge Enhancement
Edge Thresholding
Size Thresholding
Edge Gap Filling
Edge Tracking, Labeling and Feature Extraction
Component Classification
Multi-Component Classification

Logarithmic Companding of Intensity Data

A fundamental problem that is encountered in active imaging is that of clutter. Clutter is caused by specular reflections, roller marks, ground-in scale and other foreign objects. It is extremely important for the segmentation algorithms to pick out imperfections alone—and not clutter objects—in order to provide real-time performance.

Fortunately, imperfections and clutter objects are separable in terms of the intensity range in which they manifest themselves. Imperfections typically have intensities lying in the 0-50 grey level range. On the other hand, clutter objects usually have significantly higher grey level intensities.

Consequently, a pre-processing operation based on logarithmic companding of the image has been identified. Historically, companding has been successfully used in digital coding of speed in order to better utilize the available dynamic range. In our context, it represents a novel application of a classical concept. More precisely, the compensated image from the sensor is subjected to the following transformation:

$$I_t = C \log_{10}(AI_c + B)$$

In the above,
$I_c$ = compensated image intensity
$I_t$ = transformed image intensity
A,B,C = preselected constants The nature of the logarithm function is such that it expands the dynamic range in the lower intensity regions, while compressing the dynamic range in the higher intensity regions. Consequently, companding exaggerates the imperfection edges and suppresses the clutter edges. Our simulations have shown the following values to be effective for the three constants:
A = 12
B = 1
C = 100.

Figure 27B:
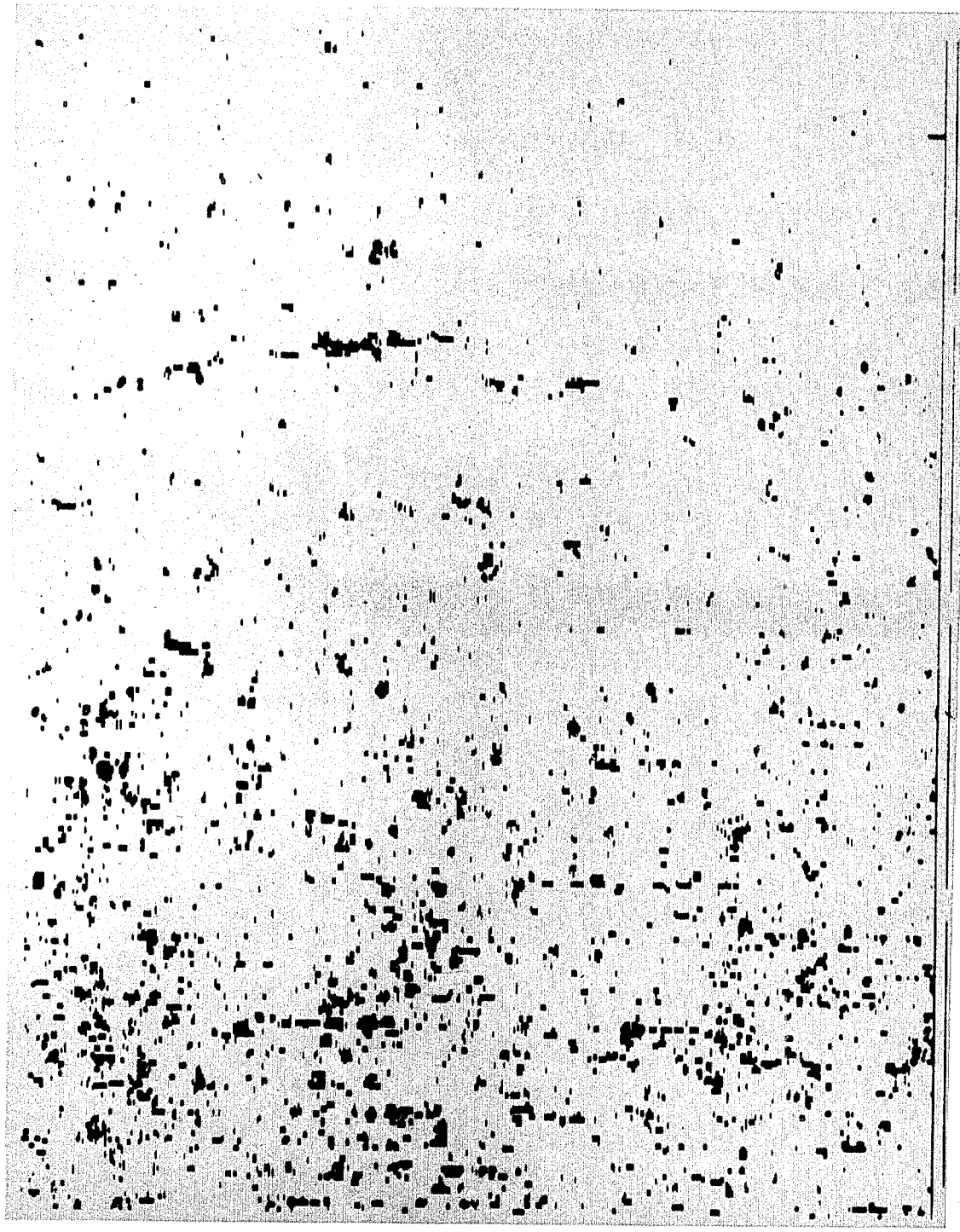
Figure 27C:
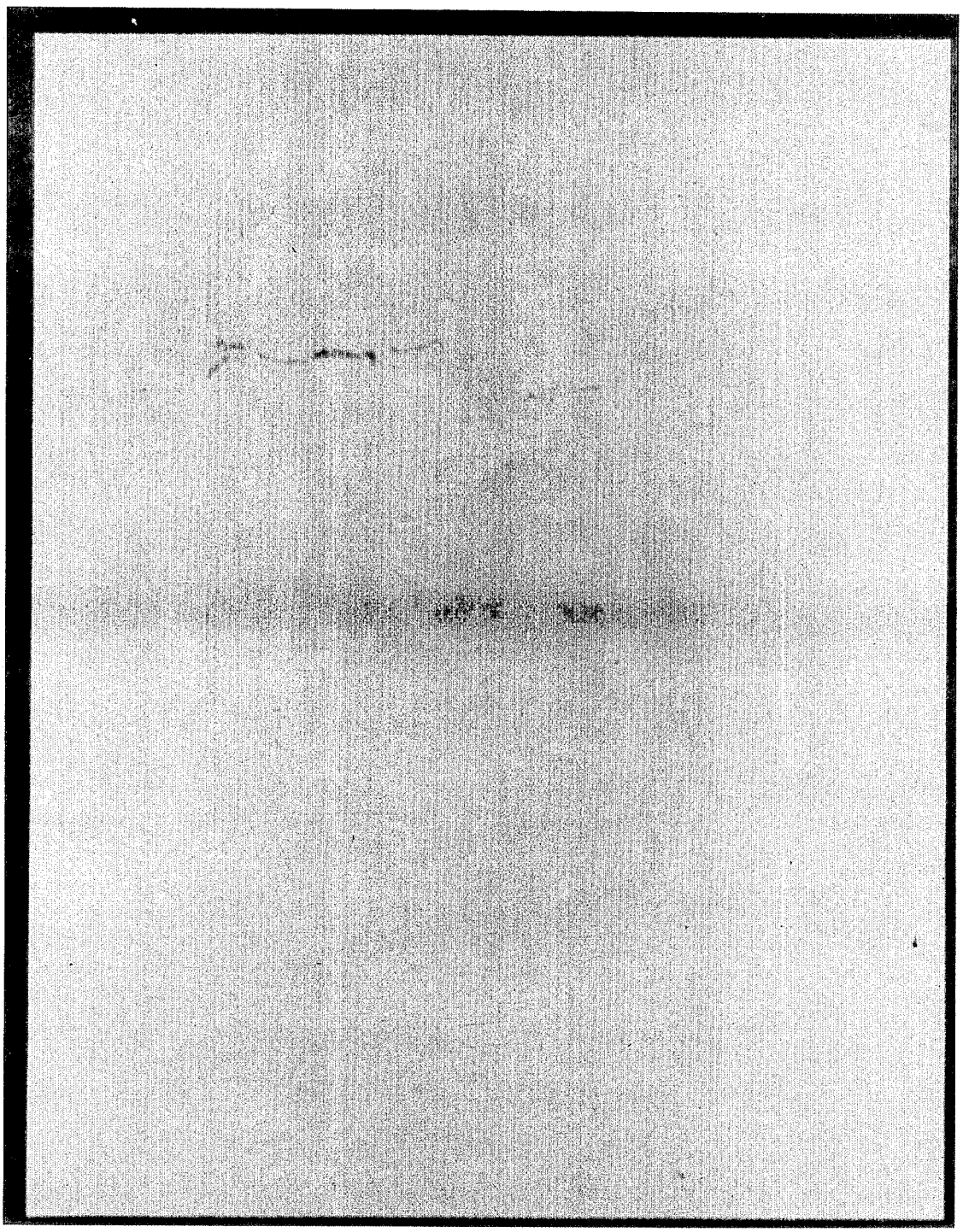
Figure 27D:
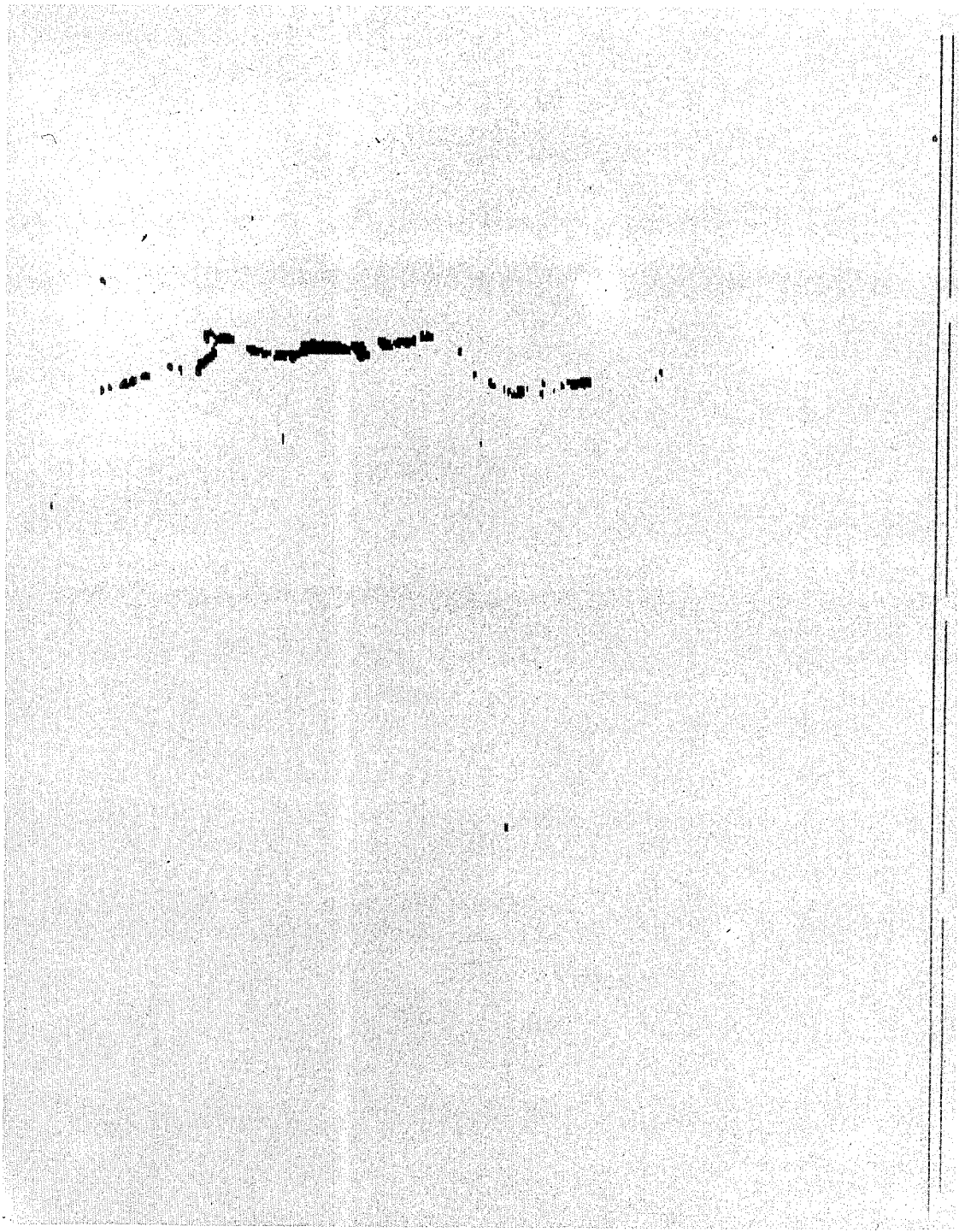

The power of the companding operation can be graphically illustrated by some examples. FIG. 27A shows the compensated image of a LFC. When this image is edge enhanced and thresholded, the result is shown in FIG. 27B. It is apparent that the segmented image has a lot of clutter. The result of log companding the image in FIG. 27A is shown in FIG. 27C. When this companded image is edge enhanced and thresholded, the result is shown in FIG. 27D. It is apparent that the LFC has been very well segmented while the clutter has been, for the most part, eliminated.

Edge Enhancement

Edge values (E) for the individual pixels are generated from the intensity data I (i, j,) with 256 grey levels. An edge enhancer found satisfactory is the Roberts gradient.

$$E(i, j) = |I(i, j) - I(i+1, j+1)| + |I(i+1, j) - I(i, j+1)|$$

Edge Thresholding

The edge value E(i, j) of a pixel is compared with a threshold $T_e$. If $E(i,j) \geq T_e$ the pixel is set equal to 1, and 0 otherwise. As explained before, fixed thresholds are applied to the first two zones on the slab surface. An adaptive threshold computed recursively is applied to the third zone.

If "i" denotes the scan line being processed and "j" denotes the pixel number on each scan line, a smoothed sum SS(i) is formed recursively for scan line i as follows:

$$SS(i) = (1 - \alpha)SS(i) + \alpha \sum_j E(j)$$

In the above, $\alpha$ is a constant which is picked such that $0 < \alpha < < 1$. The adaptive threshold for scan line $T_a(i)$ is then calculated as:

$$T_a(i) = K\{SS(i-1)\},$$

where K is a suitable constant which depends, among other things, on the extent of the third zone, as determined by the rollers in the steel mill.

Size Thresholding

After a binary image has been generated, isolated pixels are eliminated. This can be done by examining the neighbors of a particular pixel with a value 1 and zeroing the pixel if none of its neighbors has the value 1. The implementation in this format requires examination of the two adjacent scan lines as well as the present line.

Edge Gap Filling

The elimination of gaps in the binary edge image (resulting from noise) reduces the effort in both labeling and classification. Gaps in an object boundary may result in the object being split into multiple components which may hinder classification. Such gaps in the edges are anticipated because of the narrow cracks which may be only a couple pixels wide.

Edge Tracking, Labeling and Feature Extraction

Pixels associated with a particular object in the image are then labeled. This permits the structure of an individual object to be isolated from other objects. This can be done by either an edge following algorithm or an interval matching scheme. Edge following consists of first locating a pair of adjacent pixels having identical values. The search then moves in a prescribed direction depending on the transitions in the pixel value so that the edge is kept on the right until the edge is followed to the starting point. This permits the entire object to be traced but requires complicated processing to derive measures such as the area from the tracing.

Interval matching schemes establish the connectivity of intervals on adjacent scan lines of the image by their respective positions on the scan lines. Since the interval length is known it is easy to compute the area of the edge as the sum of the number of pixels in each interval. This method is complicated by the branching of the edges and the assemblance of the complete object from the edges observed on successive scan lines.

With a complete map describing the object boundaries the object can be surveyed for geometric features such as location, length, width, area, length to width ratio, orientation, etc. These features are then used by the classifier for distinguishing among the various imperfections.

From the edge intervals generated for each scan line it is necessary to devise a scheme by which all edge intervals belonging to the same object receive the same label. This is done by associating intervals of one scan line with the intervals of the previous scan line as illustrated in FIG. 7.

Because of noise and edge irregularities the problem is not as straightforward as indicated above. A narrow edge might not be present on one scan line, so association with merely the previous scan line intervals is probably insufficient for the automatic inspection of hot steel slabs. Another problem is the convergence and divergence of edges that results from cracks branching and the irregularities found in most edges. Consider the tracking of the edges in the object shown in FIG. 12.

With intervals being scanned from left to right and the interval association proceeding from top to bottom, the first interval detected will be centered about A. On a successive scan line two intervals will be found corresponding to the branches connecting A with both D and E. After a number of scan lines points B and C will show up as edge intervals and produce two branches each. At this point five intervals are being tracked for the one object and it is not until the edge intervals about D and E are detected that the connectivity of all five branches can be established.

Each edge currently being tracked is allocated to a bin which contains certain measures of the edge. These measures include the features as well as other attributes which contribute to the association between adjacent intervals.

When an interval is associated to a particular bin, that bin is updated with the new edge position along with features of the edge (e.g., area, length, straightness). Edge gap filling is handled by permitting an edge to be missed on an occasional scan line. Edge intervals which do not match with existing bins will cause a tentative bin to be initiated. If this tentative bin has no matching interval on the successive scan line it could then be deleted. This would provide a first level of length thresholding to remove sporadic intervals resulting from salt and pepper image noise.

When a particular bin is not updated for a number of successive scan lines, the object has probably ended and room must be made for new objects. At this time the bin is closed and its features are presented for classification. Since a single object may have numerous edges in a particular scan line, a chain linking scheme must be used to link all the bins resulting from edge tracking of the object.

The edge tracking and labeling algorithm initiates a bin for a component when an interval occurs on the present scan line and has extents which do not overlap the extents of any presently allocated bin. The component corresponding to the bin is then tracked as indicated in FIG. 7 from scan line to scan line by a series of (a) extension (when one bin matches one interval)

(b) splits (when one bin matches two or more intervals)

(c) merges (when two or more bins match one interval), until no intervals match the bin for a number of successive scan lines. At this time the bin is closed and the component features are transferred to the minicomputer 42 for processing so long as no remaining bin shares ownership of that feature vector.

Five thresholds can be selected by an operator which are utilized in the edge tracking and labeling algorithm. The thresholds and their uses are described below.

(1) Split width filling threshold: $(T_1)$

When two intervals are found to match a single bin

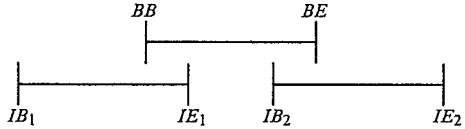

their separation $(IB_2 - IE_1)$ is compared with $T_1$. If the separation is less than $T_1$ the two intervals $([IB_1, IE_1]$ and $[IB_2, IE_2])$ are treated as one interval $[1B_1, IE_2]$. Otherwise, the tracker is prepared to allocate two bins to the component.

(2) Split Length Threshold: $(T_2)$

When the tracker is prepared to allocate two bins to the component a check is made of the present length L of the component. If $L > T_2$ the present bin is closed and two new bins and two corresponding feature vectors are allocated for the two tracks. If $L \leq T_2$ two bins are allocated each associated with the previous component.

(3) Merge Area Threshold: $(T_3)$

When one interval matches two bins, a check is made of the pixel area (PA) of each of the two components ($PA_1$ and $PA_2$). If $PA_1 > T_3$ and if $PA_2 > T_3$, the two bins are closed and a new bin and feature vector are allocated to the track. Otherwise, the features of the right bin are absorbed into feature vector associated with the left bin and the right bin is closed.

(4) Coast Length: $(T_4)$ and Width $(T_5)$ Threshold:

When a bin is missed on the present scan line a check is first made in the length L. If $L < T_4$ it is not permitted to coast and is closed. If $L \geq T_4$ a check is then made of the average width, $\overline{W}$ (pixel area divided by length). If $\overline{W} > T_5$ the bin is closed. Otherwise, it is coasted.

(5) Coast Miss Threshold: $(T_6)$

Once a bin is started coasting it is coasted until it either matches an interval again or until it has been coasted for $T_6$ scan lines. In the latter case, it is then closed.

(6) Salt and Pepper Threshold: $(T_7)$

When a component is closed, (i.e., all bins pointing to that component have been closed) a check is made of the pixel area (PA) of the component. If $PA > T_7$ the feature vector is presented to the Level 6 for classification. Otherwise it is flushed.

FEATURE VECTORS

The information to be relayed to the minicomputer 42 will include identifiers, interconnection information and geometric features which have been extracted. The elements of the feature vector are summarized as follows, some of which are indicated in FIG. 13:

(1) Component Identifier

The component identifier is an integer ranging from 1 to $2^{16}$. They are assigned sequentially to components at the time a feature vector is allocated for a particular bin.

(2) Minimum Bounding Rectangle

The $X_{min}$, $Y_{min}$, $X_{max}$, and $Y_{max}$ of the smallest rectangle enclosing the component are updated as needed on every scan line for which the component is traced. When two components merge and the decision is made to combine the features of the two components, a similar update is required.

(3) Origination and Termination Position

These are the X-values of the first and last detection points of this component. (The Y-position information is contained in the minimum bounding rectangle.) These values are only made into the feature vector at initiation, closing or merging of components and are not updated every scan line.

(4) Pixel Area

The pixel area (PA) of a component is accrued by summing the number of pixels of each interval used to update a bin allocated to that component. This is done on every scan line for every interval that is found to match.

(5) Perimeter Measures

Two perimeter measures (PER1, PER2) are accrued for each component. PER1 is associated with the left edges of a component interval while PER2 is associated with the right edges. When a bin is initiated, half the interval length is placed in PER1 and the remainder in PER2. From that point on the perimeter of left edges is accrued in PER1 and the perimeter of the right edges is summed in PER2.

If $X_{L(i)}$ and $X_{R(i)}$ are used to denote the left and right extents, respectively of the bins on the i-th scan line corresponding to a particular component, then the incremental changes in PER1 and PER2 are given by $$1 + |X_{L(i)} - X_{L(i-1)}|$$

and $$1 + |X_{R(i)} - X_{R(i-1)}|,$$

respectively.

COMPONENT CLASSIFICATION

For each object tracked by the array processor 40, a feature vector is generated and sent on to the component classifier 46 for classification. In the component classifier several more features are computed as functions of those passed from the array processor. After component classification the area imperfection feature vectors are trimmed down to only those features needed in the report program and are written out to the report file buffer in memory.

The feature vectors for the line imperfections are augmented with several features needed in the multicomponent combiner 48. These feature vectors are written to a work area in memory which is direct accessed by the multicomponent routine. After multicomponent combining, vectors which reprendent components of a single imperfection are combined into a single feature vector. This feature vector is then trimmed to "report length" and written out to the report program buffer.

Twenty three features computed in the array processor 40 are listed in Table I. The features computed in the component classifier 46 for area and line imperfections are listed in Table II. Features written out to the report file are listed in Table III.

TABLE I

| Features Computed in the Array Processor | |
|---|---|
| Feature | Definition |
| ID | Unique Identifier |
| XBEG | beginning x value |
| XEND | ending x value |
| XMIN | minimum x value |
| YMIN | minimum y value |
| XMAX | maximum x value |
| YMAX | maximum y value |
| PA | pixel area |
| NUMMED | number of median x values |
| SMPINT | sampling interval of x values |
| LASTY | y value corresponding to last median x value |
| MED1 | first median x value |
| MED2 | second median x value |
| MED3 | third median x value |
| MED4 | fourth median x value |
| MED5 | fifth median x value |
| MED6 | sixth median x value |
| MED7 | seventh median x value |
| MED8 | eighth median x value |
| MED9 | ninth median x value |
| MED10 | tenth median x value |
| RGL | right geometric length |
| LGL | left geometric length |

TABLE II

| Features Computed in the Component Classifier | | | |
|---|---|---|---|
| Area Imperfections | | Line Imperfections | |
| Feature | Definition | Feature | Definition |
| L | Length | L | Length |
| W | Width | W | Width |
| AL | Average Length | AL | Average Length |
| AW | Average Width | AW | Average Width |
| S | Slant | S | Slant |
| F | Fill | F | Fill |
| CR | Curve ratio | CR | Curve ratio |
| | | MSE | Mean square error |
| | | SRYONE | Search region first y value |
| | | SRYTWO | Search region second y value |
| | | SRXMIN | Search region minimum x value |
| | | SRXMAX | Search region maximum x value |
| | | COMPID | Component identifier |
| | | DIREC | Line orientation |
| | | CLASS | Classification |

TABLE III

| Features Written to the Report File | | |
|---|---|---|
| XBEG | XEND | XMIN |
| YMIN | XMAF | PA |
| L | W | AL |
| AW | MED1 | MED2 |
| MED3 | MED4 | MED5 |

TABLE III-continued

| Features Written to the Report File | | |
|---|---|---|
| MED6 | MED7 | MED8 |
| MED9 | MED10 | DIREC |
| CLASS | | |

A design for the component classifier 46 for a continuous slab caster involves a hierarchical type tree classifier such as the one shown in FIG. 8. Such a classifier is satisfactory because it accommodates high speed implementation and is ideally suited to exploit the distinct structural information that characterizes the slab imperfections.

The imperfections to be classified can be broadly divided into two categories which are line imperfections and area imperfections.

The imperfections falling into these two categories are illustrated in FIG. 3 and listed below. Under each category, the imperfections are listed in decreasing order of importance.

| Line Imperfections | Area Imperfections |
|---|---|
| Longitudinal Face Crack (LFC) | Scum Patch/Tear (SPT) |
| Longitudinal Corner Crack (LCC) | Broadface Bleeder (BB) |
| Transverse Face Crack (TFC) | Corner Bleeder (CB) |
| Corner and Edge Tears (CT) | Rapeseed Scab (RS) |
| Double Pour (DP) | |
| Collar Mark (CM) | |

For each object segmented in the array processor 40, certain features are extracted and sent to classifier 46 to be used in classification. These features, with reference to FIG. 13, are listed below.

(1) (XBEG, YMIN)—the coordinates of the start point in the object.

(2) (XEND, YMAX)—the coordinates of the end point in the object.

(3) (XMIN, YMIN)—the minimum X and Y coordinates of the smallest rectangle which circumscribes the object.

(4) (XMAX, YMAX)—the maximum X and Y coordinates of the smallest rectangle which circumscribes the object.

(5) LGL—the left geometric length = the perimeter of the left edge of the object.

(6) RGL—the right geometric length = the perimeter of the right edge of the object.

(7) "$(x_i, y_i)$—the set of midpoints of the width of the object on certain predetermined scan lines"; they are computed dynamically based on the rolling direction length of the imperfection rather that at fixed scan line intervals. In particular, the median x values will be recorded every 10 scan lines until an object's length exceeds 100 scan lines. At that point every other x value will be deleted (leaving only x values for every 20 scan lines) and accrual of x values will continue every 20 scan lines until the object's length exceeds 200 scan lines. At that point the procedure is iterated so that x values are being accrued every 40 scan lines, etc. In this manner every object will end up with between 1 and 10 median x values. The exact number of x values is recorded in the feature NUMMED. The distance in scan lines between x values is recorded in the feature SMPINT. LASTY contains the last y value corresponding to the last x value accrued. This information is sufficient to compute the y values corresponding to the median x values. The features MED1, . . . ,MED10 are the median x values.

(8) PA—the pixel area = the total number of pixels comprising the object. The above features are observed directly from an object segmented from the slab image. Using these, several other features are computed which are listed below.

(9) L—length = YMAX − YMIN

(10) W—width = XMAX − XMIN

(11) AL—average length = PA/W

(12) AW—average width = PA/L

(13) S—Slant = L/W

(14) F—fill = PA/(L*W)

(15) AGL—average geometric length = (LGL + RGL)/2

(16) AGW—average geometric width = PA/AGL

(17) AS—average slant = AGL/AGW

(18) MSE—mean square error of the best linear fit of the median points $(x_i, y_i)$

(19) CR—curve ration = (LGL − RGL)/AGL

The example of FIG. 13 illustrates some of these features which shows a hypothetical tracked object along with its minimum bounding rectangle. Some of the feature values are explained with reference to this object.

The hierarchical tree classifier of FIG. 8 indicates as explained above how a potential object is tracked through a series of "node classifiers", which successively narrows the field of candidates, until it is uniquely identified. It is apparent that even though there are ten different classifiers, no object will have to be processed by more than five classifiers. This feature contributes to the speed of implementation of the classifier. The logic of each of the node classifiers in detail is as follows:

Node Classifier 1

When a potential object is presented to the classifier, a decision has to be made on whether it is noise or a candidate imperfection. This decision will be made based on the area size of the object. An object will be called a candidate imperfection only if it has a certain minimum pixel area; if not, it is construed as being noise. Hence, the classification logic follows.

$PA > T_{11}$ Imperfection $< T_{11}$ Noise

Node Classifier 2

Figure 14A:
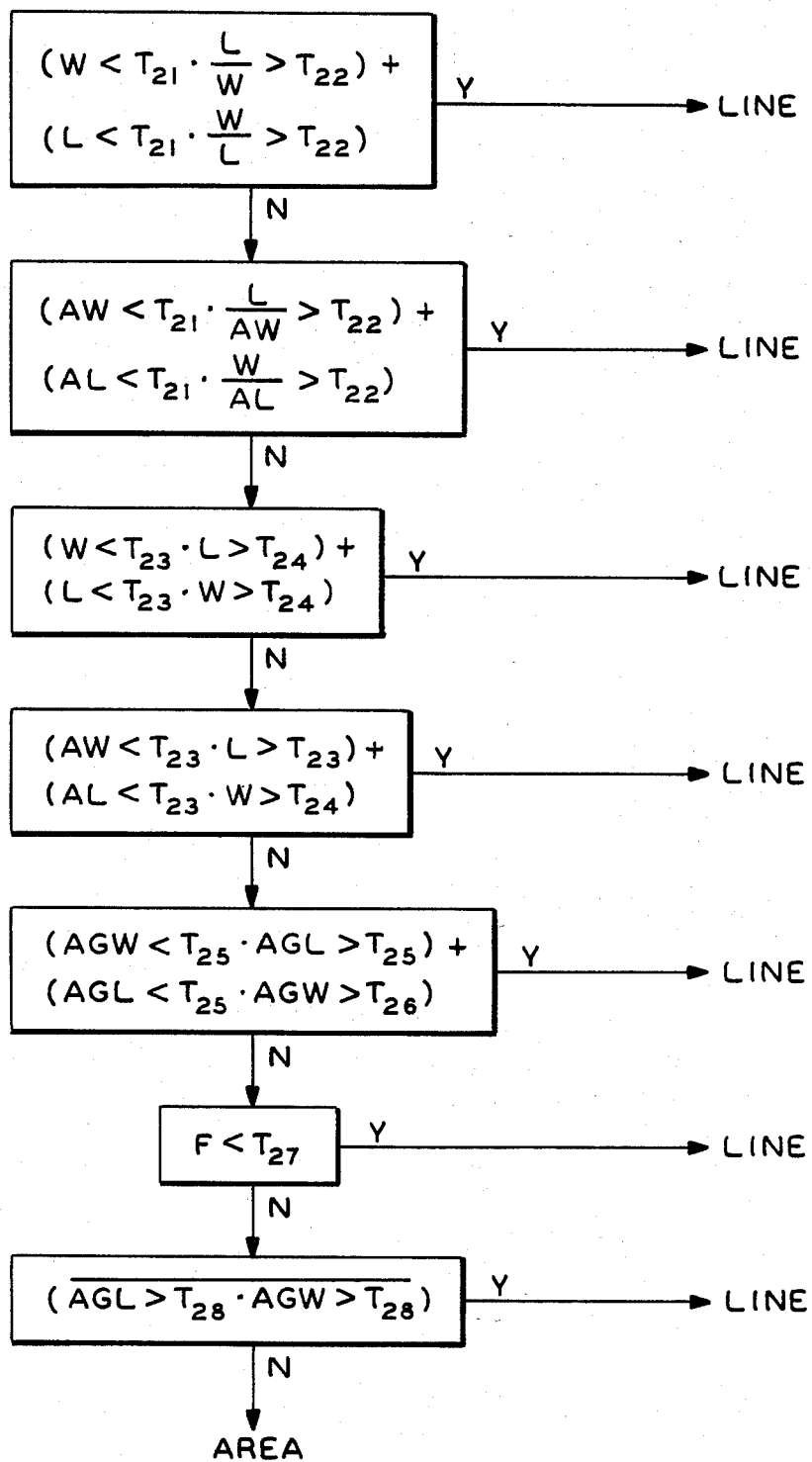
FIGS. 14A to 14I show classifier logic for nodes of the hierarchial tree flow chart of FIG. 8.

Node Classifier 2 performs a coarse classification and characterizes each imperfection as being either of the line type or the area type. Line imperfections have the characteristic that they typically have one dimension several times larger than the other dimension. Area imperfections tend to fill their minimum bounding rectangles better than do line imperfections. FIG. 14A shows the classifier logic for node 2.

Node Classifier 3

Figure 14B:
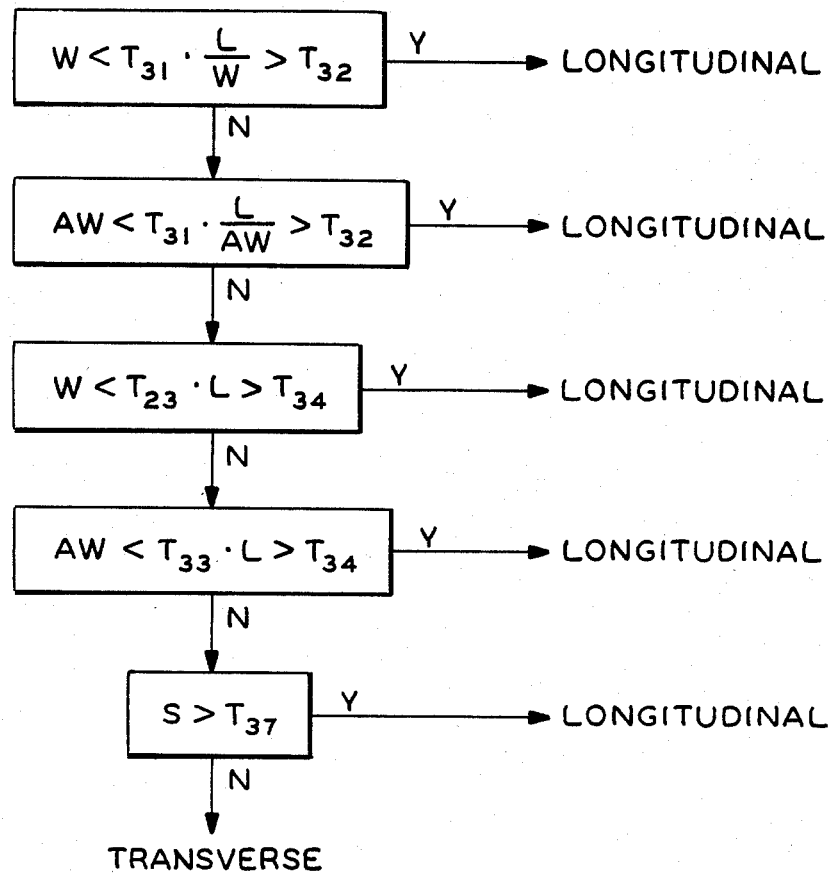

Node Classifier 3 is designed to distinguish between line imperfections with longitudinal orientation and line imperfections with transverse orientation. The logic for it is shown in FIG. 14B.

Node Classifier 4

Figure 14C:
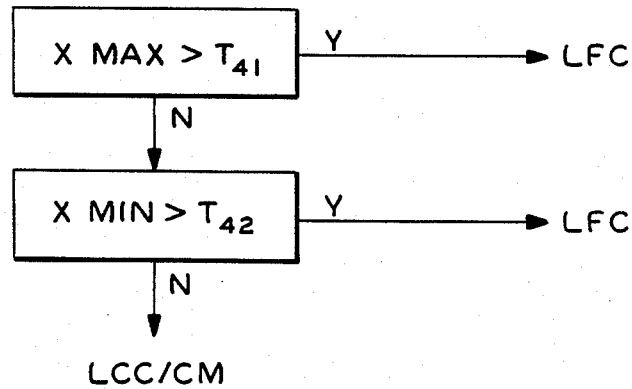

Node Classifier 4 is designed to recognize longitudinal face cracks. The other two longitudinal imperfections, i.e., longitudinal corner cracks and collar marks, are relegated to the next stage for classification. The criterion for classification here is that longitudinal face cracks are well removed from the corner of the slab. The logic for it is shown in FIG. 14C.

Node Classifier 5

Figure 14D:
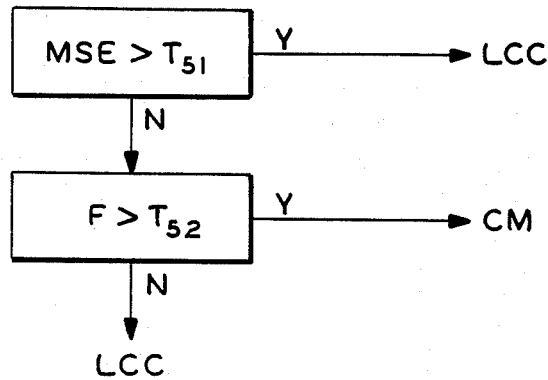

Node Classifier 5 is intended to distinguish between longitudinal corner cracks and collar marks. Both of these imperfections are situated close to the corner of the slab. Relatively speaking, however, collar marks are ramrod straight, while longitudinal collar cracks tend to wander around. The logic for it is shown in FIG. 14D.

Node Classifier 6

Figure 14E:
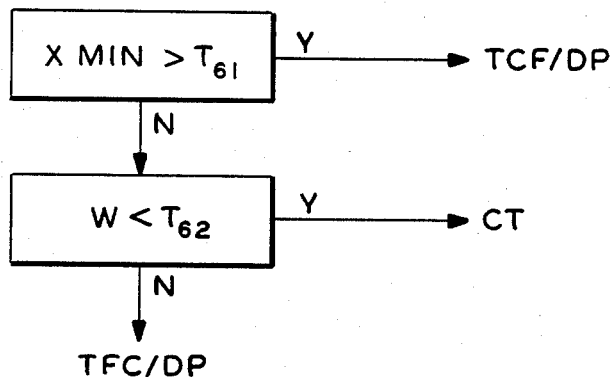

Node Classifier 6 is designed to recognize corner tears while rejecting transverse face cracks and double pours. Corner tears are relatively short in length and are located close to the corner of the slab. The logic for it is shown in FIG. 14E.

Node Classifier 7

Figure 14F:
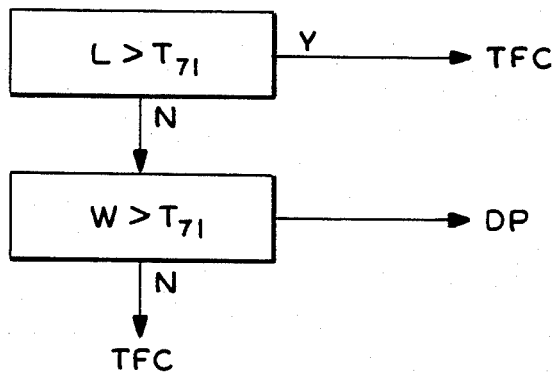

Node Classifier 7 distinguishes between double pours and transverse face cracks. Double pours are very large, extend across the width of the slab and around. Since the current system will not be examining the entire width of the slab, we must guess as to whether the imperfection runs all the way across. Further, transverse face cracks can wander considerably in the longitudinal direction, while double pours generally do not. The logic for it is shown in FIG. 14F.

Node Classifier 8

Figure 14G:
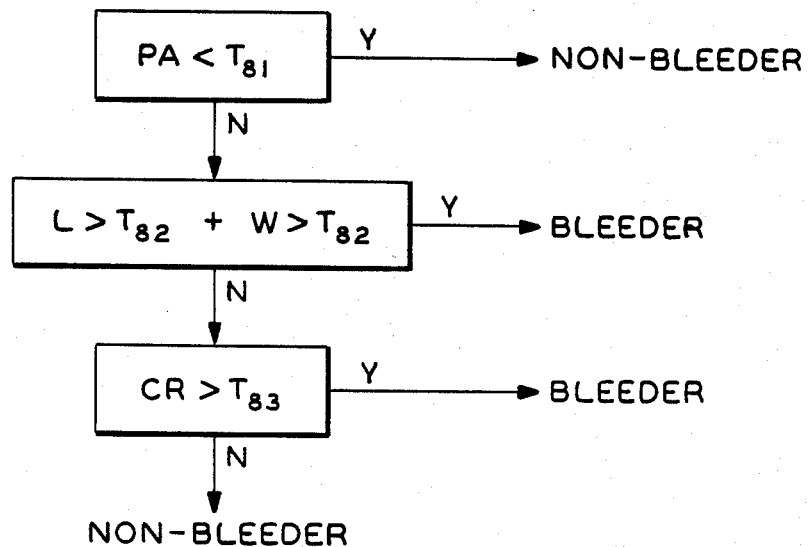

Node Classifier 8 distinguishes bleeder imperfections from non-bleeder imperfections. Bleeders are characterized by large areas and large linear dimensions. Further, bleeders have a distinct curvature due to their crescent shaped outline. The logic for it is shown in FIG. 14G.

Node Classifier 9

Figure 14H:
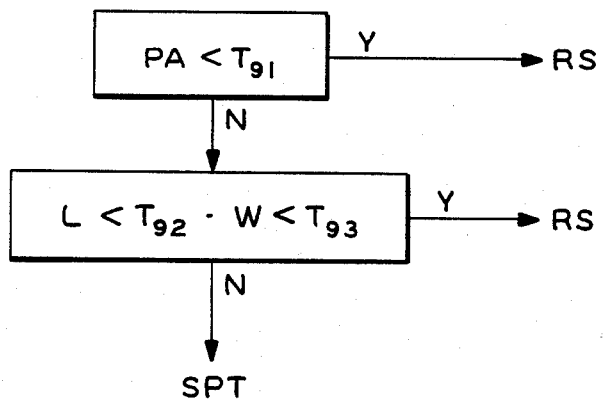

Node Classifier 9 further classifies non-bleeder imperfections as being either rapeseed scabs or scum patches/tears. Rapeseed scabs are physically much smaller than scum patches/tears. The logic for it is shown in FIG. 14H.

Node Classifier 10

Figure 14I:
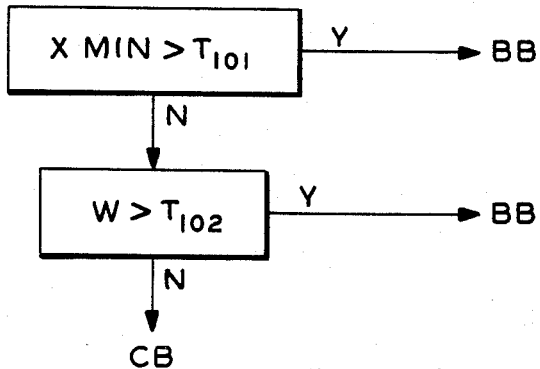

Node Classifier 10 distinguishes corner bleeders from broadface bleeders. Corner bleeders are situated close to the corner of the slab, while broadface bleeders are located away from the corner. The logic for it is shown in FIG. 14I.

In a test run of the component classifier 46, excellent results were obtained.

Figure 15:
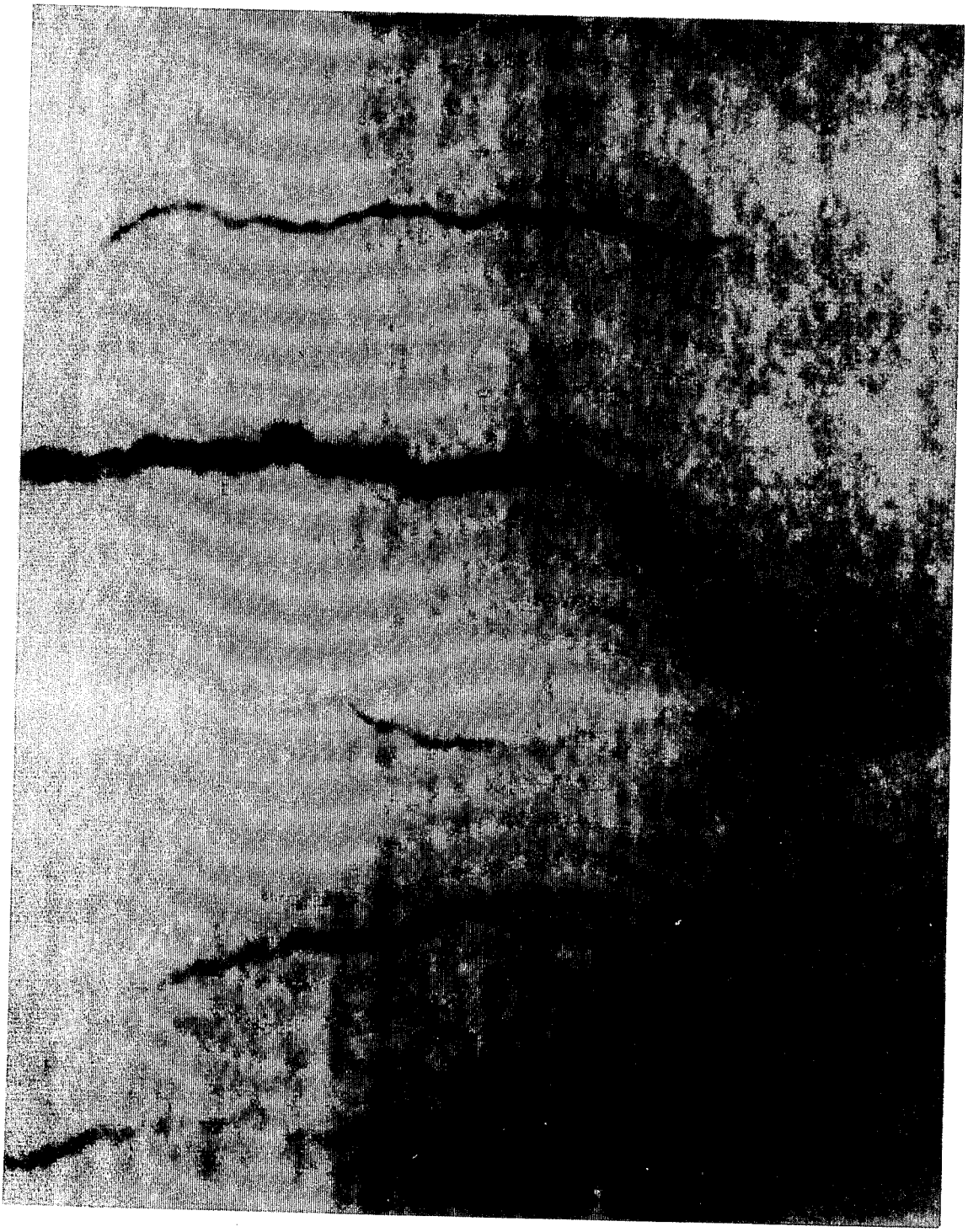
FIG. 15 shows an original image of a slab with a number of cracks.
Figure 16:
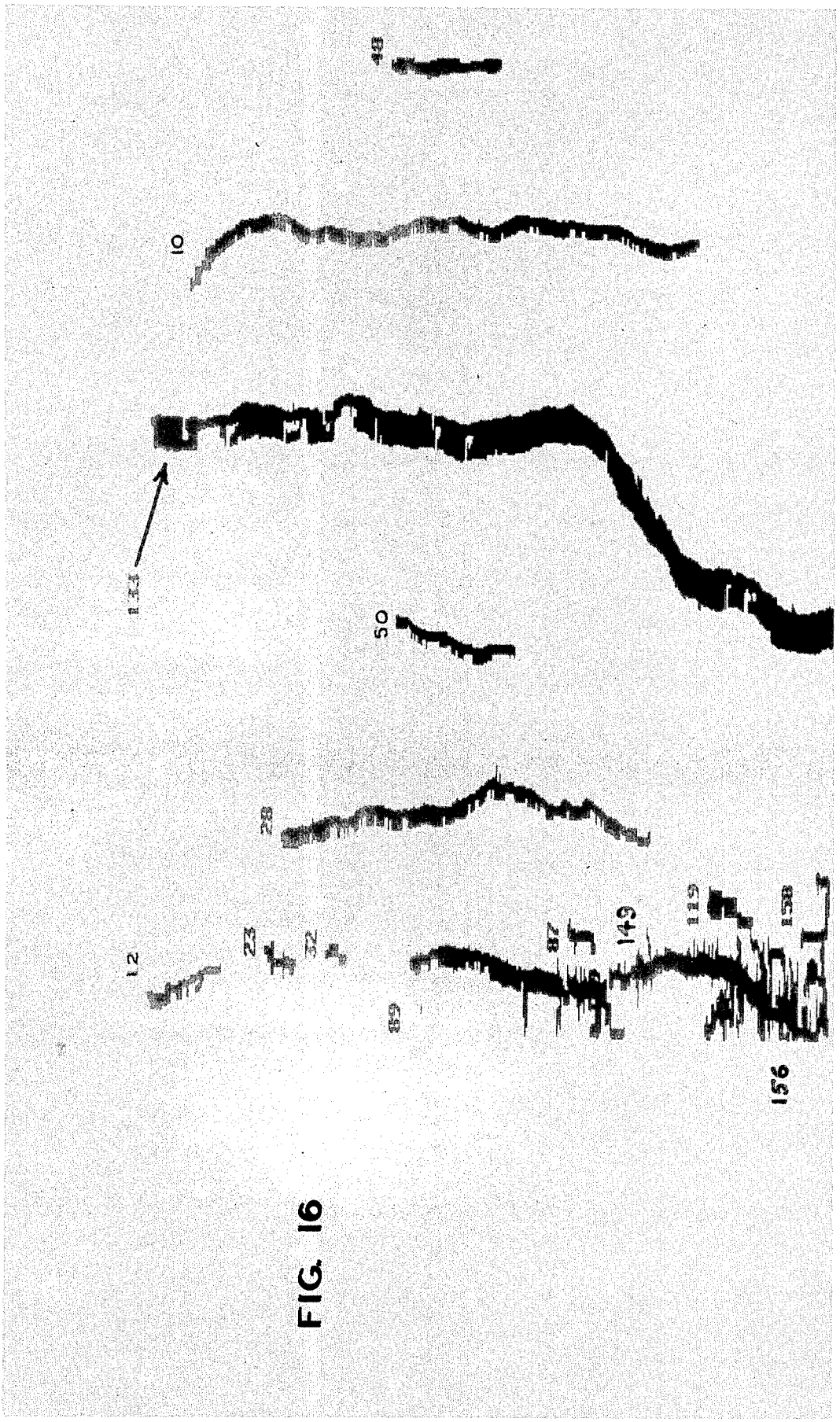
FIG. 16 shows a segmented, labeled image of the slab of FIG. 14.

FIG. 15 shows the original image with a number of cracks. The segmented, labeled image is shown in FIG. 16. The output of the component classifier is shown in the following Table IV.

TABLE IV

| IDENTIFIED IMPERFECTIONS | |
|---|---|
| OBJECT ID | CLASS |
| 12 | LCC |
| 23 | RS |
| 32 | RS |
| 48 | LFC |
| 50 | LFC |
| 87 | RS |
| 89 | LCC |
| 28 | LFC |
| 10 | LFC |
| 119 | RS |
| 149 | LCC |
| 156 | RS |
| 158 | TFC |
| 133 | LFC |

LCC - Longitudinal Corner Crack
RS - Rapeseed Scab
LFC - Longitudinal Face Crack
TFC - Transverse Face Crack

MULTI-COMPONENT SYNTACTIC/SEMANTIC CLASSIFIER

The purpose of the multi-component classifier is, as referred to above, to reconstruct imperfections which may have been fragmented during the data collection or segmentation processes, and hence classified as a series of distinct imperfections by the component classifier. For instance, due to high thresholding in the array processor 40, a single longitudinal crack might appear as several distinct cracks laid end to end. The same phenomenon might occur if the crack became narrow at several points that the sensing apparatus could not perceive continuation of the crack. The reconstruction herein is directed to cracks and certain crack-line imperfections. These are longitudinal face and corner cracks, collar marks, corner tears, transverse face cracks, and double pours. These are denoted respectively as LFC, LCC, CM, CT, TFC and DP.

The task may be broken into three stages. The first is to identify sets of imperfections which are close enough together that they could possibly represent a single imperfection. This is accomplished via the proximity search procedure.

The second step is to construct syntactic symbol strings which reflect the geometric configuration of the individual sets of proximate imperfections. At this stage it is also convenient to insert obvious conditional checks to eliminate unlikely combinations of imperfections. One then saves the time involved in sending these strings to the multi-component classifier proper, where they would be eliminated from consideration anyway.

The third stage is the actual syntactic classifier wherein the strings complied in the previous stage are processed to determine which, if any, imperfections should be combined into one.

Proximity Search Procedure for Multi-Component Analysis

After individual imperfections found on the slab have been classified, it is necessary to specify a region around each one in which to search for other (already classified) imperfections. For a longitudinal crack, for instance, we could specify a region around it which is half again as long and as wide as the circumscribing rectangle. It is reasonable to search such a region for continuation of the crack further up or down the slab. For the purpose of outlining the search algorithm we will assume that with each imperfection classified, some reasonable rectangular search region has been associated.

Figure 18:
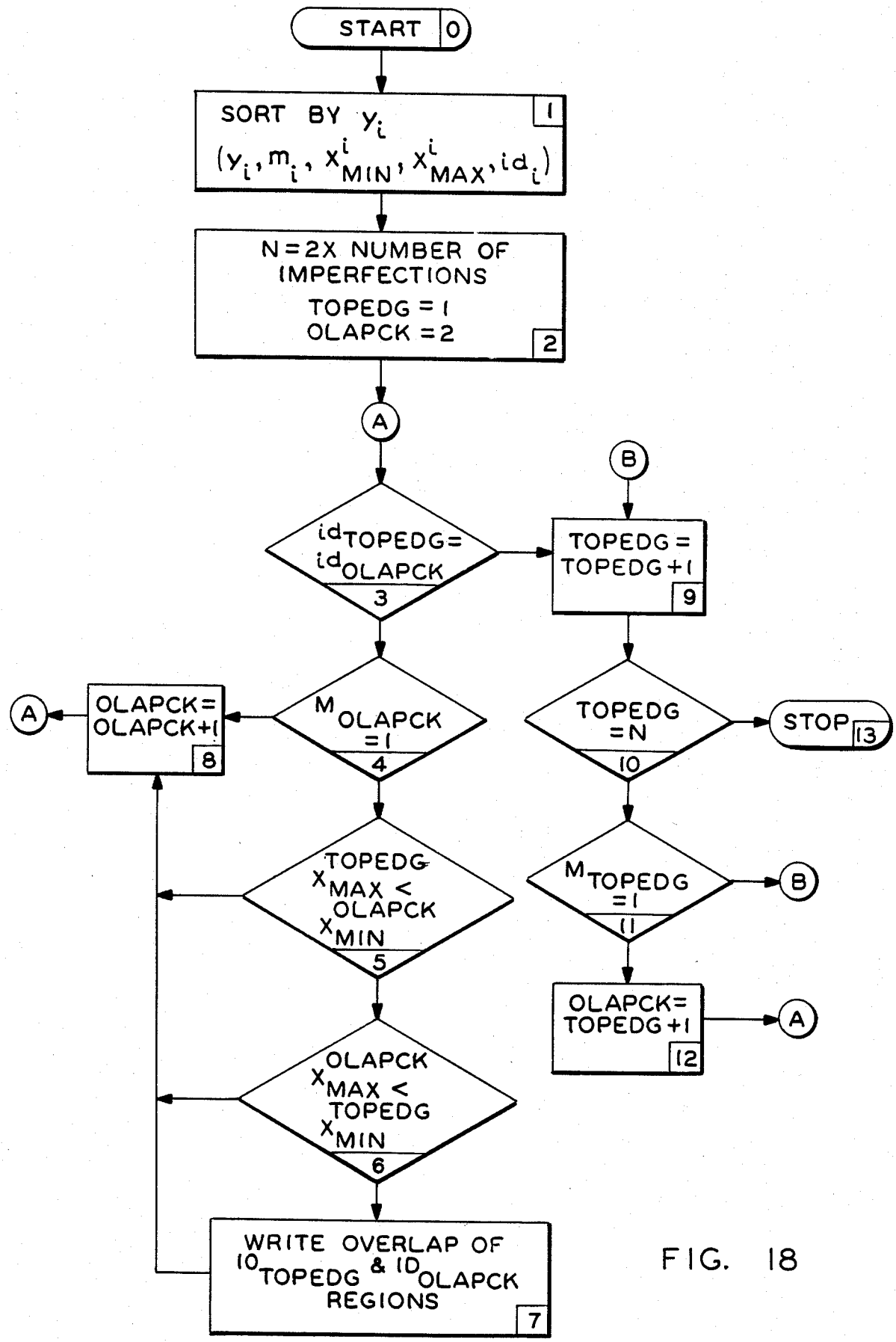
FIG. 18 illustrates a flow chart for the proximity search algorithm.

FIG. 17 illustrates search regions for a multicomponent classifier analysis and FIG. 18 illustrates a flow chart for the proximity search algorithm.

If two search regions (rectangles) are found to overlap, as indicated in FIG. 17, this information is sent to the syntactic classifier 48 for multicomponent analysis. The problem presented is to make an efficient search of the many regions to check for overlaps. Naively checking the bounds of every rectangle against every other rectangle is an order $8n^2$ operation where n=number of imperfections found on the slab.

We make the assumption that search does not commence until the slab has been completely tracked. The complexity of the algorithm varies from n to $4n(n-1)$ depending on how much overlapping is encountered.

Before presenting the algorithm we will establish some notation. The information coming into the search routine is the feature vectors of each object classified. The feature vector contains, among other data, the object identifier (id), and the extents of the search region: $X_{min}$, $Y_{min}$, $X_{max}$, and $Y_{max}$. These should not be confused with the extents of the circumscribing rectangle. In the following algorithm, we will be making lists of features, some of which will not distinguish a min Y coordinate from a max Y coordinate. The letter m will carry the min-max information: m=0 implies the y value it is associated with is a min; m=1 implies the y value it is associated with is a max.

For two objects $id_1$ and $id_2$ the min and max extents might be as illustrated in FIG. 17 where superscripts denote id association, not powers. Note that the condition "$id_1$ search region intersects $id_2$ search region" may be verified by establishing that $$(x_{min}^1 \leq x_{min}^2 \leq x_{max}^1 \text{ or } x_{min}^1 \leq x_{max}^2 \leq x_{max}^1)$$

and $$(y_{min}^1 \leq y_{min}^2 \leq y_{max}^1 \text{ or } y_{min}^1 \leq y_{max}^2 \leq y_{max}^1)$$

an illustration which accounts for all the overlap possibilities is shown in FIG. 17B.

To check for overlap in the y-direction could require up to four comparisons. Checking for "not overlap" in the y-direction requires at most two comparisons, namely $$y_{max}^1 < y_{min}^2$$

or $$y_{max}^2 < y_{min}^1$$

Therefore, in this algorithm we check for absence of overlap, as in boxes 5 and 6 of the flow chart of FIG. 18.

We will explain the algorithm via a detailed exposition of its associated flow chart shown in FIG. 18 in which the sections detailed below refer to this figure.

(a) Box 1

From each feature vector we construct two 5-tuples of numbers. The last three entries—$x_{min}^i$, $x_{max}^i$, $id_i$—are common to both 5-tuples. They are, respectively, the minimum and maximum extents in the x-direction of the search region for the object, and $id_i$ is the identifier of this object. $Y_i$, $m_i$ are, for one of two 5-tuples, the minimum y-coordinate of the search region and $m_i=1$. In other words, $m_i$ is the flag for the two 5-tuples associated to the $i^{th}$ object, which indicates whether the first coordinate of the 5-tuple is a minimum or maximum y extent of the search region for the $i^{th}$ object.

We sort all of the 5-tuples into one list as follows:

$$(y_i, m_i, x_{min}^i, x_{max}^i, id_i) < (y_j, m_j, x_{min}^j, x_{max}^j, id_j)$$

if $$[y_i < y_j]$$

or if $$[y_i = y_j \text{ and } m_i \leq m_j]$$

Figure 19A:
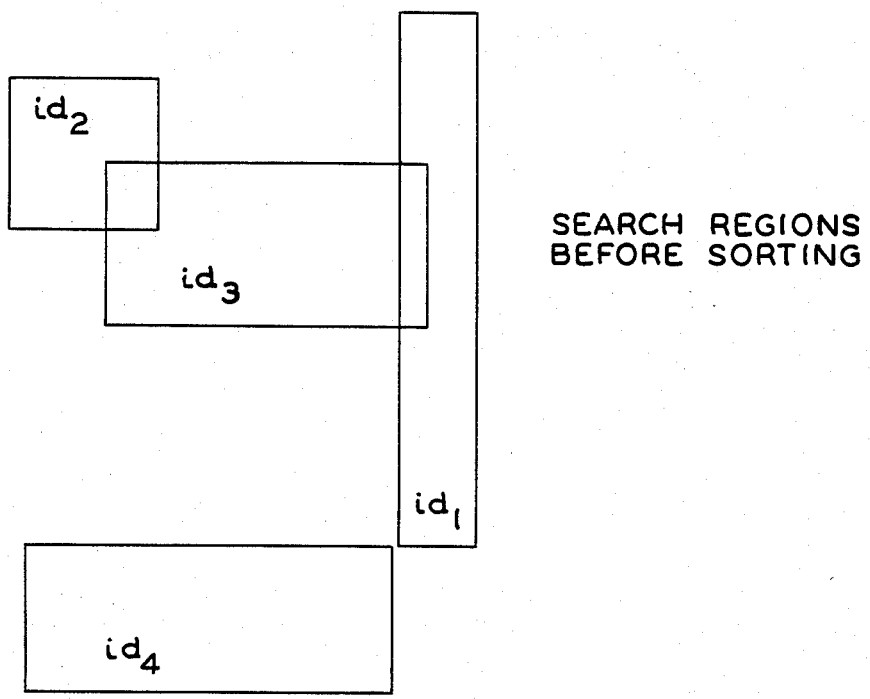
FIGS. 19A and 19B illustrate examples of sorting search regions.
Figure 19B:
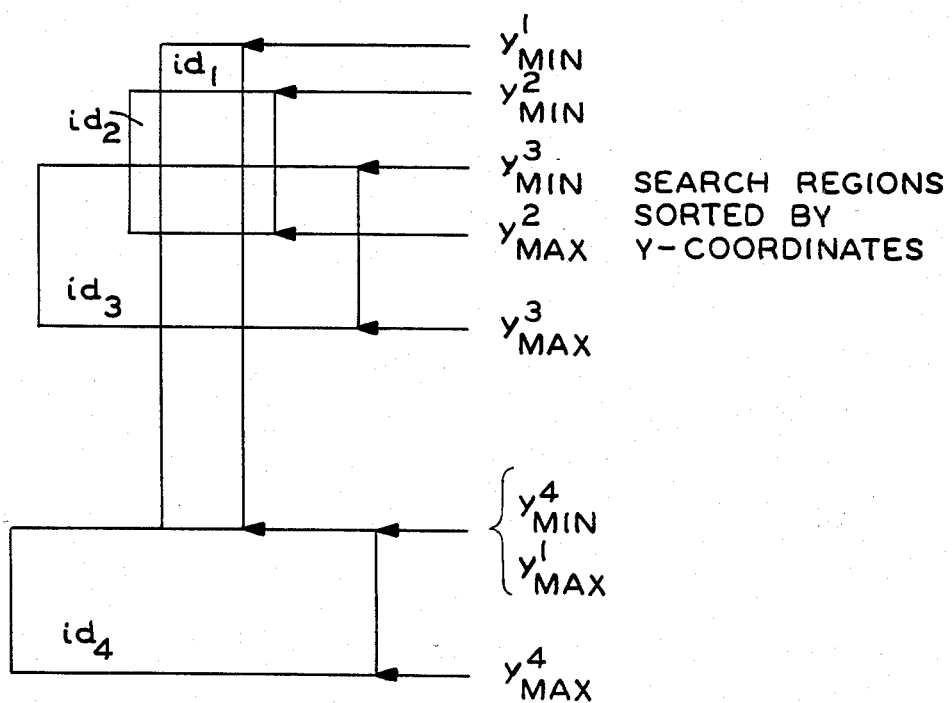

Geometrically, this ordering lines up the search regions according to their extent in the y-direction. FIG. 19 illustrates the effect of this sorting procedure. FIG. 19A pictures hypothetical search regions as they might actually occur on a slab. FIG. 19B shows them sorted in the y-direction.

(b) Box 2

N is the number of 5-tuples in the sorted list. It is used as a check to see if all objects on the slab have been processed. The algorithm will proceed by fixing the $y_{min}$ of a search region—its "top edge", and sequentially checking each region which overlaps it in the y-direction to see if it also overlaps in the x-direction. TOPEDG will point to the basic region we have fixed, while OLAPCK ("overlap check") will point to a region which overlaps the basic region in the y-direction and is currently being checked against the basic region for a direction overlap. The identifier for the basic region will then be $id_{TOPEDG}$, so that initially it is $id_i$, the identifier of the first object in the list. The identifier for the overlap check region will be $id_{OLAPCK}$, initially equal to $id_2$.

(c) Box 3

If two 3-tuples have the same identifier, then $Y_{TOPEDG}$ is $Y_{min}$ for the object with that identifier and $Y_{OLAPCK}$ $Y_{max}$ for the same object. This means that the next 5-tuple in the list corresponds to a search region which either does not overlap $id_{TOPEDG}$ or has already been checked for overlap. So it is unnecessary to check any other regions for overlap with $id_{TOPEDG}$, since no others can overlap $id_{TOPEDG}$'s region in the y-direction. This is the point where the power of the sorted list is being exploited to save many operations. The "yes" branch will be followed in part (f). If the id's are not equal we have encountered a region which potentially overlaps that corresponding to $id_{TOPEDG}$. We must now check it for overlap.

(d) Boxes 4 and 8

If $M_{OLAPCK}=1$ then y is the $y_{max}$ for the search region corresponding to $id_{OLAPCK}$. This means we have already checked $id_{OLAPCK}$ against $id_{TOPEDG}$. Either $y_{TOPEDG}^{min} < y_{OLAPCK}^{min} < y_{OLAPCK}^{max} < y_{TOPEDG}^{max}$, in which case we have already detected $y_{OLAPCK}^{min}$ before, or else $y_{OLAPCK}^{min} \leq y_{TOPEDG}^{min} \leq y_{OLAPCK}^{max} \leq y_{TOPEDG}^{max}$ in which case there was a previous iteration where $y_{TOPEDG} = y_{OLAPCK}^{min}$ and the search regions were compared. So if $M_{OLAPCK}=1$ we do not need to check for overlap again and we proceed to increment OLAPCK and return to part (c) where $id_{TOPEDG}$ will be compared against $id_{OLAPCK}$ now the next item in the list. The "no" branch is handled in part (e).

(e) Boxes 5, 6, 7 and 8

At this point we know that $y_{min}^{TOPEDG} \leq y_{min}^{OLAPCK} \leq y_{max}^{TOPEDG}$ and so the $id_{TOPEDG}$ and $id_{OLAPCK}$ regions overlap in the y-direction. To check for overlap in the x-direction requires up to four comparisons; namely, $$x_{min}^{TOPEDG} \leq x_{min}^{OLAPCK}$$

and $$x_{min}^{OLAPCK} \leq x_{max}^{TOPEDG}$$

or $$x_{min}^{OLAPCK} \leq x_{max}^{TOPEDG}$$

and $$x_{max}^{TOPEDG} \leq x_{max}^{OLAPCK}$$

However, to check for not overlapping requires a maximum of two comparisons; namely, $$x_{max}^{TOPEDG} < x_{min}^{OLAPCK}$$

or $$x_{max}^{OLAPCK} < x_{min}^{TOPEDG}$$

Naturally, we utilize the latter. If both of these comparisons are false, then the regions overlap and we write this information out, increment OLAPCK, and return to part (c).

If either comparison is true, the regions associated to $id_{TOPEDG}$ and $id_{OLAPCK}$ do not overlap, and so we proceed immediately to increment OLAPCK and return to part (c).

(f) Boxes 3, 9, 10, 11, 12, 13

If $id_{TOPEDG} = id_{OLAPCK}$ then, as explained in part (c) we have already checked every region which possibly overlaps $id_{TOPEDG}$. Hence, we proceed to increment TOPEDG.

If TOPEDG=N we have reached the last object on our list and so we are done.

If TOPEDG≠N, we then check to see if $y^{TOPEDG}$ is a $h_{max}$. If so, we return to node (B) and increment TOPEDG again. If not, we have found the next $y_{min}$ in the list. We then set OLAPCK to be the first 5-tuple in the list after the new TOPEDG and return to part (c). This completes the algorithm.

This algorithm may be modified slightly in order to do the proximity search procedure in parallel with the tracking of the slab. Begin by collecting some minimum numbe of search regions (say 50) from the slab. Allow others to pile up in a queue. Process the 50 regions just as in the case already outlined. That is, sort them by y coordinates and walk down the list making the appropriate comparisons. Now pick up exactly one more region from the queue, and sort it into the list. Set TOPEDG=$y_{min}$ of the new region and do the algorithm (walk down the list) until OLAPCK=$y_{max}$ of the new region. At this point, instead of incrementing TOPEDG, return to the queue and set exactly one more region. Continue until a "no more regions on slab" flag is found in the queue.

Output of Proximity Search Procedure

In measuring a slab, it may be the case that widely separated "clusters" of imperfections may be found by the search procedure. It is undesirable for the multicomponent syntactic classifier 48 to compare imperfections between these clusters, since we already know that these disparate groups of imperfections cannot represent a single imperfection. To avoid unneeded processing, we write output from the proximity search procedure to a series of different disk files. Each output file contains only the feature vectors of imperfections which appear in one cluster. The syntactic classifier will use these files as input, but will process them separately.

Since the output of the search procedure is the input to the syntactic classifier, some processing relevant to string construction is done at this stage. If two imperfections are found to have overlapping search regions, several conditions relating specific features of these imperfections will be checked. The nature of these conditions will be explained in the section on string construction. If the two imperfections fulfill the necessary criteria, their feature vectors will be written out to the currently opened output file.

String Construction

A "string" is any ordered list of imperfections. String construction is itself accomplished in two steps. The first occurs in the output phase of the proximity search procedure. Here the conditional checks mentioned in the proximity search procedure will be detailed. The second step occurs at the front end of the syntactic classifier proper, and involves constructing syntactic "sentences", or symbol strings, from the output of the proximity procedure.

Step 1: String Construction—Recall that the proximity search procedure associates imperfections in sets of two. We insert the following conditional checks at this point.

(a) If either of two imperfections is not of our family slated for potential reconstruction, (i.e., if either is not an LFC, LCC, CM, CT, TFC, or DP) then we write nothing to the syntactic classifier input file.

(b) If we have two close cracks of the same orientation (either both transverse or both longitudinal) then we check if either they are end to end, or if they overlap significantly and are roughly parallel. The latter check is necessary since a wide crack might be perceived as two parallel cracks situated close to one another. If either condition holds then we write out the string TFC1+TFC2 or LCC1+LFC2 etc. to the syntactic classifier input file. Otherwise nothing is written.

(c) If we have two close cracks of different orientation, we check to see if they are end to end before writing them out, since no imperfection has a fragment with a "T" or "1" shape in it.

To determine the condition "end to end" we check the distance of (XEND, YEND) to (XBEG, YBEG) for longitudinal imperfections, while for transverse imperfections we check the distance of $$\text{MIN}(\text{ABS}(\text{XMAX}/-\text{XMIN2}), \text{ABS}(\text{XMAX2}-\text{XMIN1})).$$

If this distance is less than an appropriate threshold, then we conclude that the imperfections are roughly end to end. Here, (XEND, YEND) is the bottom most point of the upper imperfection. (XBEG, YBEG) is the topmost point of the lower imperfection while XMIN1, XMAX1, XMIN2, XMAX2 correspond to the minimum and maximum extents of the first and second imperfections in the x-direction. These measurements are illustrated in FIG. 20.

To determine the condition "overlap significantly" for transverse cracks we use the following scheme. First we find the amount the two cracks overlap in the x-direction. OVERLAP=MIN (XMAX1, XMAX2)−MAX (XMIN1, XMIN2). Note that if OVERLAP is less than zero, this indicates that the cracks do not overlap at all, but are in fact separated by ABS(OVERLAP). Now let SUM=(XMAX1−XMIN1)+(XMAX2−XMIN2) and % OVERLAP=(OVERLAP/SUM-OVERLAP)×100. Then % OVERLAP measures what percent of the two cracks overlap. We threshold % OVERLAP to determine if the two cracks could have been opposite edges of a thick crack. If this is reasonable (say % OVERLAP=75) then we proceed with the check for parallelism.

The measure slant=S=L/W=LENGTH/WIDTH where LENGTH=length of the circumscribing rectangle and WIDTH=width of the circumscribing rectangle of an imperfection, determines the greatest average slant that an imperfection could have. Comparing the relative slants of two imperfections yields a measure of how parallel they are. We use the normalized differences of the slants of two imperfections to measure parallelism:

ABS (S1−S2)

where S1 and S2 are the slants of two different imperfections. This is illustrated in FIG. 21.

The following Table V is a list of all binary strings, that is, strings of length two, which could possibly be output from the search procedure for input to the syntactic classifier. The "condition" column gives the condition which must be fulfilled in order for the string to be output. Here EE means "end to end" and OP means "overlap and parallel". The "merge" column lists the possible results of combining the two imperfections into one. Note that some strings like CT+CM or LCC+DP are not present because they do not correspond to realizable fragments of known imperfections.

TABLE V

| Binary Strings Input to Syntactic Classifier | | |
|---|---|---|
| BINARY STRINGS | CONDITION | MERGE |
| LFC + LFC | EE or OP | LFC |
| LFC + LCC | EE or OP | LCC |
| LFC + CM | EE | LFC |
| LFC + CT | EE | LCC |
| LFC + TFC | EE | slant dependent |
| LCC + LFC | EE or OP | LCC |
| LCC + LCC | EE or OP | LCC |
| LCC + CM | EE | LCC |
| LCC + CT | EE | LCC |
| LCC + TFC | EE | slant dependent |
| CM + CM | EE or OP | CM |
| CM + LCC | EE | LCC |
| CM + LFC | EE | LFC |
| CT + CT | EE or OP | CT or TFC |
| CT + LFC | EE | LCC |
| CT + LCC | none | LCC |
| CT + TFC | EE | TFC or DP |
| CT + DP | none | DP |
| TFC + CT | EE | TFC or DP |
| TFC + DP | none | CP |
| TFC + TFC | EE or OP | DP or TFC |
| TFC + LFC | EE | slant dependent |
| TFC + LCC | EE | slant dependent |

Step 2: String Construction—The second step of the string construction algorithm occurs at the front of the syntactic classifier. Here a set of binary strings must be arranged into a single string. This is done as follows. Let a,b,c represent 3 different imperfections. Let the concatenation of any two of the symbols (i.e., ab, ba, ac, ca, bc, cb) represent a binary string written as output from the search procedure. We then combine binary strings into longer strings by this mapping:

(ab, ab)→ab (ab, ba)→ba (ab, bc)→abc (ab, cb)→acb (ab, ac)→abc (ab, ca)→cab

The (already combined) longer string is combined with a binary string in an analogous manner. For example, (abc, bd)→abcd continuing in this fashion until there are no more binary strings to combine into the string.

Syntactic Classifier

If we list all conceivable ways an imperfection we expect to encounter could possibly be broken up into smaller pieces, each of which would be interpreted by the component classifier as a single imperfection, we find that each such fragmentation can be written as an ordered list or string, of adjacent imperfections. For instance, a single transverse face crack might appear as, say, three adjacent transverse face cracks. Denoting a transverse face crack by the symbol TFC, we write this string as TFC1+TFC2+TFC3. Then, working backwards, we may construct what the output from the proximity search procedure for this set of imperfections will be. In the example above, the search procedure might find that TFC1 and TFC2 are close, and that TFC2 and TFC3 are close. It is possible to now reverse the process outlined; given the results of the search procedure, we can reconstruct the string TFC1+TFC2+TFC3. The syntactic classifier could then use a look-up table to tell us that these should be combined into a single transverse face crack. The problem here is that, theoretically, at least, a string could be arbitrarily long. We might encounter, for instance, a longitudinal corner crack the entire length of a slab which appears as 10 or 20 or 100 short cracks strung out end to end. We cannot have look-up tables of arbitrary length. Instead, the syntactic classifier is designed as follows.

We fix some very large maximum allowable string length, say 1000, which we do not expect any string encountered to exceed. Then the space of 1000 words is set aside in the memory of computer 42 and we reconstruct a string from the search procedure output, as outlined previously, and store it in this workspace. Now we examine this string "two words" at a time, and keep track of any intermediate combinations. For our example, cited previously, we would first consider TFC1 and TFC2. Presumably these cracks are either end to end or roughly parallel, or else we would never have written the string out from the search procedure. Now a look-up table (in which each entry is only two words long)

tells us these two should be combined into one TFC. Now we tag these two with the same I.D. number and proceed to send TFC2 and TFC3 into the look-up table. Again, the table indicates that these two are to be combined into one TFC. Since TFC3 now has the same I.D. as TFC2 which has the same I.D. as TFC1, the three all have the same I.D. even though TFC1 was never compared with TFC3. At this point we update the imperfection class code, if applicable. Hence the slab report writing program will list these as one (updated) imperfection.

Figure 22:
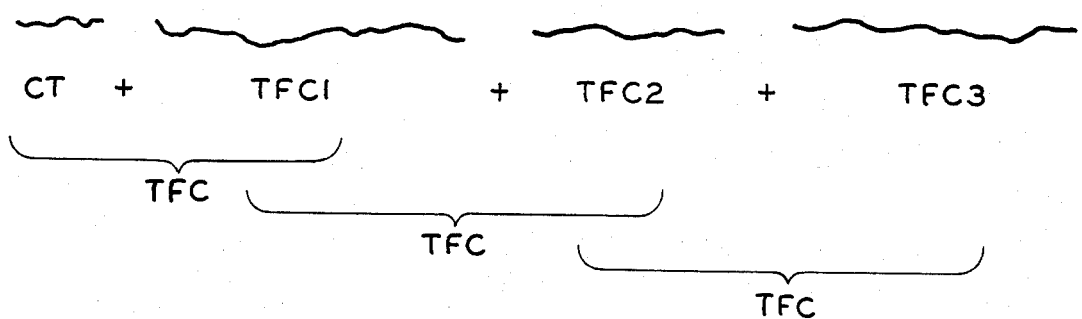
FIG. 22 illustrates the process of parsing an imperfection string.

Now the classifier would look for the imperfection following TFC3. Since there is none it would now look at the total combined imperfection. Because a double pour can appear as a sequence of TFC's all end to end, the classifier would now check if the combined width of these was the full slab width. If so, it would change the class code on these objects all to double pour, and then write them out to a report file. If not, they would be reported as a TFC. This process is summarized in FIG. 22.

Examination of all strings corresponding to conceivable fragmentations of imperfections indicates that in all but two cases the decision to merge two imperfections (or not to merge them) can be made immediately. The exceptions are LFC+TFC and LCC+TFC. In these cases it is necessary to observe a third imperfection, either LCC or LFC, in order to combine the three into one LCC or LFC. This corresponds to the fragmentation of the longitudinal crack pictures in FIG. 23. Note that the string LFC+TFC (or LCC+TFC) without a following LCC or LFC does not correspond to fragmentation of a single crack, but should remain as two distinct imperfections.

Note that in the case or combinations of transverse and longitudinal imperfections which are end-to-end, e.g., TFC+LFC, the slant of the combined imperfection must be thresholded to determine if it should be considered an LFC or TFC.

SLAB IMPERFECTION REPORT

Reference is made to the format for the line printer slab inspection report illustrated on a sample slab with two imperfections shown in FIG. 4 and in the following sample slab report.

Sample Slab Report

MILL: Gary
DATE: 1/28/81
TIME: 14:15:28
SLAB ID
    Heat Number: H001-01
    Cut Number: 500
IMPERFECTION: A
TYPE: LONGITUDINAL FACE CRACK
START COORDINATES: 5.55, 20.85
END COORDINATES 8.10, 42.70
IMPERFECTION SIZE
    Length: 30.30
    Width: 0.69
    Depth: 0.90
    Area: 20.80
IMPERFECTION: B
TYPE: CORNER TEAR
START COORDINATES: 23.16, 22.35
END COORDINATES: 25.40, 23.85
IMPERFECTION SIZE
    Length: 2.24
    Width: 0.20
    Depth: 0.40
    Area: 0.41

Length, width, and depth are reported in the usual sense, namely, length is the extent of the long direction of a crack and width is the extent of the short direction of a crack. The correspondence of these physical attributes of imperfections to the features computed by the classifier is given in Table VI shown in FIG. 23. The formulae used to compute physical attributes of area imperfections and to compute depth are also listed. The definitions of the features L, W, AW and PA are referred to previously herein. The calculation of depth is as indicated and area is computed by direct conversion of the feature "pixel area" (PA) to square inches.

When components are merged into a single imperfection by the multicomponent classifier, their physical attributes must be merged appropriately. The formulae for calculating the merged physical attributes are given in Tables VIIa and VIIb shown in FIGS. 24A and B, depending on whether the imperfections being merged are end to end or overlapping and parallel. These conditions are referred to above in connection with the discussion of the classifier.

Decisions on the disposition of slabs are based on the information summarized in Tables VIIIa, VIIIb and VIIIc shown in FIGS. 25A, B and C depending on whether the slab is intended for sheet, tin mill, or D and I.

SYSTEM HARDWARE

The inspection process disclosed herein calls for the real time classification of surface imperfections from optical images. This requires a processing system which can handle high data rate, on the order of 500K pixels/sec. for example.

An embodiment of the system had a 546K pixels/sec. data rate providing two microseconds of processing time per pixel.

In this system the array processor 40 receives image data in a scan line stream and outputs labeled objects and their associated features to the minicomputer 42 in which single and multiple component classification is done.

The array processor has three independent processors and associated buses and permits simultaneous 1/0 operations and processing. The array processor performs image processing operations on a scan line basis in real-time, and extracts feature values of potential imperfections on the slab surface. These feature values are then transmitted to the host computer 42 for identification of the imperfections.

The algorithms for the inspection process are divided between the array processes 40 and the computer 42 as shown in FIG. 5.

The high data rate into the array processor 40 is on the order of 500K pixels/sec. based on a 2048 element camera, a slab velocity of 4 inches per second and 0.015 inches between scan lines. A new scan line (2048 pixels) occurs roughly every 4 milliseconds. This means the front end processing of a pixel can take only 2 microseconds. This small amount of available time (per pixel) allows only about 10 or 20 instructions to be completed in a 200 nanosecond array processor (depending on the program and machine architecture).

The array processor 40 performs I/O operations "hidden" from the Roberts gradient. This is possible because the processor 40 contains three independently programmable processing elements and associated memory banks. A block diagram of the hardware of this structure is shown in FIG. 26. The elements of interest of the array processor are the arithmetic processing unit 50 (APU), the central signal processing unit 52 (CSPU) and the I/O scroll 54.

The array processor operates in a manner so that the APU thereof processes alternating banks of high speed (170 nanosecond) data memory. The I/O device (scroll) loads up memory plane 3 with 8 lines (8×2K bytes) of raw data.

In parallel, the APU extracts edge intervals from the data previously loaded in memory plane 2 and transfers a list of intervals to a circular buffer on plane 1 for each pair of lines processed. Upon finishing the processing of plane 2, the APU awaits the completion of the loading of the last line of raw data into plane 3 by the I/O scroll. The APU then processes the last line of raw data in plane 2 with the first line of raw data in plane 3. This "straddling" of the two memory planes provides the necessary overlap line (because Roberts gradient utilizes two adjacent lines). The APU and I/O scroll then switch memory planes and resume processing, continually observing this double buffering protocol. This ability of the array processor to receive data in one memory while processing another memory proved critical in the real-time execution of the edge filtering and is made possible by the three separate memory busses.

The medium data rate into an intermediate processor is approximately 10K pixels/sec. An entire scan line of 2048 pixels may contain only 20-30 edge transitions when highlighted by a first derivative operation such as the Roberts gradient. This corresponds to a bandwidth reduction by a factor of 50 (as each interval is characterized by both its beginning and end). Subsequent algorithms are then within the capability of a less powerful (1 microsecond) processor. The array processor has the CSPU 52 for that purpose. The CSPU 52 has the capabilities of a stand-alone minicomputer. It can typically perform an instruction in 1 microsecond and usually functions with slower (500 ns) memory. Memory plane 1 is envisioned as the permanent resident for this slower memory. The array processor support software resides in this memory in addition to user-coded algorithms.

These algorithms direct the CSPU 52 to reference the next interval list from the circular buffer in plane 1 and compare it to the current tracked interval list. The circular buffer is continuously updated by APU writes of newly derived interval lists. Comparison to the current bin interval list results in either new objects being tracked (new bins being initiated), current objects being tracked (bin updates) or old objects being terminated (bins closed). Upon closing the bin, the features that characterize it (e.g., location, length, average width, orientation, edge straightness, etc.) will be sent to the host computer 42 for classification.

The first priority of the CSPU 52 is to control the I/O ports and the APU50. This task takes less than half a millisecond for every 4 millisecond period between successive scan lines. The remaining 3.5 milliseconds can be used for bin matching and bin updating. The time required to match edge interval to the previously tracked edge intervals (bins) has been benchmarked at 22 microseconds. Bin updating was conservatively estimated at 78 microseconds. The total of 100 microseconds per tracked edge interval suggests that 30 edge intervals (bins) could be tracked simultaneously in the available three msec of remaining CSPU time. Again, this tracking is transparent to the APU because of the architecture featuring three separate memory busses and multiple independently programmed processors.

A low data rate into the host minicomputer 42 is anticipated. The host computer will be a one microsecond machine. The host 42 is assigned the most complex data processing algorithm (the classifier), yet the least arithmetic manipulations because in addition to the classification it must have time for peripheral updates. At the anticipated input rate the computer 42 would have approximately 2000 instructions in which to classify the object.

Overall, the tightest bottleneck appears to be the input to the array processor. Fortunately, this is a suitable area in which to apply high-speed fixed algorithm hardware such as the Roberts and Sobel operators. They look very much alike in hardware and either would require only one card of electronics to implement.

The embodiments of the invention in which an exclusive property or right is claimed are defined as follows:

1. A method for the real time automatic detection and classification of characteristic type surface imperfections occurring on the surfaces of material of interest comprising the steps of;
   transversely scanning a relatively moving surface of said material of interest with data generating means to sense the light intensities of scanned pixels and generating signals indicative of the sensed intensities of said scanned pixels;
   converting said signals to corresponding digital values to form a digital image of said surface and storing said digital values;
   edge enhancing said digital image formed by said digital values with an edge enhancement operator on the fly to form an edge enhanced image containing intervals of said image corresponding to the edges of said surface imperfections;
   thresholding said edge enhanced image to segment out said edges to form a thresholded image;
   interval matching said thresholded image to establish connectivity of intervals on adjacent scan lines and bin tracking connected ones of said interval (threshold image) to track and segment out imperfection objects formed by said edges;
   forming object feature vectors by computing and accruing directly determinable features including an object identifier of each of said objects; and
   classifying said objects with the aid of said features into characteristic type surface imperfections.

2. The method according to claim 1 wherein said data generating means is a data camera and said generated signals are voltage signals.

3. The method according to either of claims 1 or 2 wherein said scanning, edge enhancement and interval matching and bin tracking are accomplished on a scan line basis.

4. The method according to claim 3 wherein said scan lines are contiguous.

5. A method for the real time automatic detection and classification of characteristic type surface imperfections occurring on the surfaces of material of interest, comprising the steps of;
   transversely scanning lines of a relatively moving surface of said material with a data camera to sense the light intensities of scanned pixels and generating voltage values which correspond to the sensed intensities of said scanned pixels;

converting said voltage values to corresponding digital values to form a digital image of said surface and storing said digital values;

edge enhancing said digital image formed by said digital values with an edge enhancement operator on the fly on a scan line basis to form an edge enhanced image comprising scan lines containing intervals of said image corresponding to the edges of said imperfections;

thresholding said edge enhanced image to segment out said edges and form a thresholded image;

interval matching said threshold image to establish connectivity of intervals on adjacent scan lines and bin tracking connected one of said intervals (threshold image) on a scan line basis to track and segment out objects formed by said edges;

forming object feature vectors by computing and accruing directly determinable features including an object identifier of each of said objects including a unique identification, pixel area and boundaries thereof; and classifying said objects with the aid of said features into characteristic type surface imperfections.

6. The method according to either of claims 1 or 5 wherein said step of forming object features further comprises:

forming primary features including a unique identification, pixel area and boundaries thereof;

computing secondary features from said primary features including length, width, and slant of said objects.

7. A method according to either of claims 1 or 5 including the step of outputting data in the form of a report identifying classes of discovered imperfections and information with regard to sizes and locations of said imperfections, wherein said information is in human readable form.

8. A method according to either of claims 1 or 5 wherein said light intensities of said pixels result from reflected light from said surface.

9. A method according to either of claims 1 or 5 including the step of companding said digital image to minimize background clutter.

10. A method according to claim 9 wherein the step of companding includes logarithmically companding said digital image to minimize background clutter by expanding the dynamic range in the lower intensity region harboring imperfections to exaggerate the imperfection edges and compressing the dynamic range harboring background clutter to suppress the clutter edges.

11. A method according to either of claims 1 or 5 wherein pixels equal to or larger than the threshold value are set equal to 1 and to 0 if less than said threshold.

12. A method according to either of claims 1 or 5 wherein variable adaptive thresholding is utilized.

13. A method according to either of claims 1 or 5 wherein said classifying of objects is implemented by a hierarchal tree classifier.

14. A method according to claim 13 wherein said hierarchal tree classifier has binary statistical classifiers.

15. A method according to either of claims 1 or 5 wherein said material of interest is metal in slab form and further comprising the step of automatically making slab disposition decisions, said step comprising;

establishing slab disposition determining dimensions of the physical attributes of different kinds of said imperfections and storing said dimensions; and comparing said computed features with said dimensions to make an automatic slab disposition decision based on the results thereof.

16. A method according to either of claims 1 or 5 including the step of comparing classified objects on the basis of proximity searches to make a determination of the presence of sister components of larger objects and combining revealed related sister components to form larger objects upon finding sets of related sister components; and appropriately classifying newly revealed ones of said larger objects.

17. A method according to claim 15 including the step of comparing classified objects on the basis of proximity searches to make a determination of the presence of sister components of larger objects and combining revealed related sister components to form larger objects upon finding sets of related sister components; and appropriately classifying newly revealed ones of said larger objects.

18. A method according to claim 16 wherein syntactic/semantic rules are used in connection with said determination.

19. A method according to claim 17 wherein syntactic/semantic rules are used in connection with said determination.

20. A method according to claim 18 wherein strings of potential objects are formed and spatial tests are made for said strings as prerequisites for combining objects.

21. A method according to either of claims 1 or 5 wherein one of the said feature extraction techniques involves an approximating technique wherein recorded interval data is discarded on a line skipping basis in proportion to the length of an object being tracked and during the time the object is tracked.

22. A method according to either of claims 1 or 5 wherein said interval matching and bin tracking involves an approximating technique wherein for each interval recorded only the data corresponding to the midpoint of each said interval is retained to represent an edge of a tracked object.

23. An apparatus for the real time automatic detection and classification of characteristic type surface imperfections occurring on the surfaces of material of interest comprising;

means for transversely scanning contiguous lines of a relatively moving surface of said material of interest with a data generating means to sense the light intensities of scanned pixels and generating signals indicative of the sensed intensities of said scanned pixels;

means for converting said signals to corresponding digital values to form a digital image of said surface and storing said digital values;

means for edge enhancing said digital image formed by said digital values with an edge enhancement operator on the fly to form an edge enhanced image containing intervals of said image corresponding to the edges of said surface imperfections;

means for thresholding said edge enhanced image to segment out said edges to form a thresholded image;

means for interval matching said thresholded image to establish connectivity of intervals on adjacent scan lines and means for bin tracking connected ones of said intervals (thresholded image) to track and segment out imperfection objects formed by said edges;

means for forming object feature vectors by computing and accruing directly determinable features including an object identifier of each of said objects;

means for classifying said objects with the aid of said features into characteristic type surface imperfections.

24. An apparatus for the real time automatic detection and classification of characteristic type surface imperfections occuring on the surfaces of material of interest, comprising of the following elements;

means for transversely scanning lines of a relatively moving surface of said material with a data camera to sense the light intensities of scanned pixels and generating voltage values which correspond to the sensed intensities of said scanned pixels;

means for converting said voltage values to corresponding digital values to form a digital image of said surface and storing said digital values;

means for edge enhancing said digital image formed by said digital values with an edge enhancement operator on the fly on a scan line basis to form an edge enhanced image comprising scan lines containing intervals of said image corresponding to the edges of said imperfections;

means for thresholding said edge enhanced image to segment out said edges to form a thresholded image;

means for interval matching said thresholded image to establish connectivity of intervals on adjacent scan lines and bin tracking connected ones of said intervals (thresholded image) on a scan line basis to track and segment out objects formed by said edges;

means for forming object feature vectors by computing and accruing directly determinable features of each of said objects including a unique identification, pixel area and boundaries thereof; and means for classifying said objects with the aid of said features into characteristic type surface imperfections.

* * * * *